US011086317B2

(12) United States Patent
Healey et al.

(10) Patent No.: US 11,086,317 B2
(45) Date of Patent: Aug. 10, 2021

(54) EMOTIONAL ADAPTIVE DRIVING POLICIES FOR AUTOMATED DRIVING VEHICLES

(71) Applicant: Intel Corporation, Santa Clara, CA (US)

(72) Inventors: Jennifer Healey, San Jose, CA (US); Victor Palacios Rivera, Guadalajara (MX); Ignacio Alvarez, Portland, OR (US)

(73) Assignee: Intel Corporation, Santa Clara, CA (US)

(*) Notice: Subject to any disclaimer, the term of this patent is extended or adjusted under 35 U.S.C. 154(b) by 389 days.

(21) Appl. No.: 15/941,303

(22) Filed: Mar. 30, 2018

(65) Prior Publication Data

US 2019/0049957 A1 Feb. 14, 2019

(51) Int. Cl.
*G05D 1/00* (2006.01)
*G05D 1/02* (2020.01)
(Continued)

(52) U.S. Cl.
CPC ......... *G05D 1/0066* (2013.01); *A61B 5/0077* (2013.01); *A61B 5/024* (2013.01);
(Continued)

(58) Field of Classification Search
CPC .. G05D 1/0066; G05D 1/0257; G05D 1/0246; G05D 1/0221; G05D 1/0088; G05D 2201/0213; G06N 3/08; G06N 3/006; G06N 3/0454; B60W 30/16; B60W 30/10; B60W 50/0098; B60W 40/08; B60W 2556/50; B60W 2556/00; B60W 2555/00; B60W 2540/21; B60W 2050/0088; B60W 2710/20; B60W 2710/18; B60W 2720/24;
(Continued)

(56) References Cited

U.S. PATENT DOCUMENTS

2006/0149428 A1 7/2006 Kim et al.
2011/0224875 A1 9/2011 Cuddihy et al.
(Continued)

FOREIGN PATENT DOCUMENTS

CN 111448117 A 7/2020

OTHER PUBLICATIONS

Myounghoon Jeon (2017) Emotions in Driving, Chapter in Emotions and Affect in Human Factors and Human-Computer Interactions, Academic Press, 624 pages (12 page abstract included).
(Continued)

*Primary Examiner* — Ian Jen
(74) *Attorney, Agent, or Firm* — Schiff Hardin LLP

(57) ABSTRACT

In one example a system for emotional adaptive driving policies for automated driving vehicles, comprising a first plurality of sensors to detect environmental information relating to at least one passenger in a vehicle and a controller communicatively coupled to the plurality of sensors and comprising processing circuitry, to receive the environmental information from the first plurality of sensors, determine, from the environmental information, an emotional state of the at least one passenger, and implement a driving policy based at least in part on the emotional state of the at least one passenger. Other examples may be described.

23 Claims, 16 Drawing Sheets

(51) Int. Cl.
| | |
|---|---|
| *B60W 40/08* | (2012.01) |
| *B60W 50/00* | (2006.01) |
| *A61B 5/00* | (2006.01) |
| *A61B 5/024* | (2006.01) |
| *A61B 5/16* | (2006.01) |
| *A61B 5/18* | (2006.01) |
| *G01C 21/34* | (2006.01) |
| *G06N 3/04* | (2006.01) |
| *B60W 30/10* | (2006.01) |
| *G06N 3/00* | (2006.01) |
| *B60W 30/16* | (2020.01) |
| *G06N 3/08* | (2006.01) |

(52) U.S. Cl.
CPC ............... *A61B 5/165* (2013.01); *A61B 5/18* (2013.01); *A61B 5/6893* (2013.01); *B60W 30/10* (2013.01); *B60W 30/16* (2013.01); *B60W 40/08* (2013.01); *B60W 50/0098* (2013.01); *G01C 21/3484* (2013.01); *G05D 1/0088* (2013.01); *G05D 1/0221* (2013.01); *G05D 1/0246* (2013.01); *G05D 1/0257* (2013.01); *G06N 3/006* (2013.01); *G06N 3/0454* (2013.01); *G06N 3/08* (2013.01); *A61B 5/4803* (2013.01); *A61B 5/7264* (2013.01); *B60W 2040/089* (2013.01); *B60W 2040/0872* (2013.01); *B60W 2050/0088* (2013.01); *B60W 2400/00* (2013.01); *B60W 2420/42* (2013.01); *B60W 2420/52* (2013.01); *B60W 2420/54* (2013.01); *B60W 2540/21* (2020.02); *B60W 2540/22* (2013.01); *B60W 2555/00* (2020.02); *B60W 2556/00* (2020.02); *B60W 2556/50* (2020.02); *B60W 2710/18* (2013.01); *B60W 2710/20* (2013.01); *B60W 2710/30* (2013.01); *B60W 2720/24* (2013.01); *G05D 2201/0213* (2013.01)

(58) Field of Classification Search
CPC ......... B60W 2540/22; B60W 2420/54; B60W 2420/52; B60W 2420/42; B60W 2400/00; B60W 2040/089; B60W 2040/0872; B60W 2710/30; B60W 2540/221; G01C 21/3484; A61B 5/6893; A61B 5/18; A61B 5/165; A61B 5/024; A61B 5/0077; A61B 5/7264; A61B 5/4803
See application file for complete search history.

(56) References Cited

U.S. PATENT DOCUMENTS

| | | |
|---|---|---|
| 2015/0246673 A1 | 9/2015 | Tseng et al. |
| 2017/0140270 A1 | 5/2017 | Mnih et al. |
| 2017/0140279 A1 | 5/2017 | Turgeman |
| 2018/0022361 A1 | 1/2018 | Rao et al. |
| 2018/0189581 A1* | 7/2018 | Turcot ............... G06K 9/4628 |
| 2020/0064146 A1* | 2/2020 | Kitajima ............. G01C 21/362 |

OTHER PUBLICATIONS

Jokinen, K., McTear, M. Spoken Dialogue Systems (2010) Morgan and Claypool,151 pages (Abstract included). http://www.morganclaypool.com/doi/abs/10.2200/S00204ED1V01Y200910HLT005.

Rosalind W. Picard, (1997) Affective Computing, MIT Press Sep. 1997, 306 pages. ISBN: 9780262161701 https://mitpress.mit.edu/books/affective-computing (Abstract included).

Winter, Kathy, "Passengers have a lot to say about self-driving cars—we should listen", in Intel Newsroom, Editorial, Oct. 18, 2017.

NY Times, Joshua brown tested the limits of his tesla, extracted Online on Oct. 10, 2017, 5 pages.

Abraham, H. et all, What's in a Name: Vehicle Technology Branding & Consumer Expectations for Automation in Proceedings of Automotive UI '17, Sep. 24-27, 2017, Oldenburg, Germany, 11 pages.

Sung et al., (2010) Domestic Robot Ecology: an initial framework to unpack long-term acceptance of robots ad home. Int. J Soc. Robot 2(4), 417-429, 14 pages.

André, E., Dybkjær, L. Neumann, H. Pieraccini, R.. and Weber, M. (2008) Perception in Multimodal Dialogue Systems. IEEE Jun. 2008 (Abstract included).

Shalev-Shwartz et all (2017) On a formal Model of Safe and Scalable Self-driving Cars, downloaded from: https://arxiv.org/pdf/1708.06374.pdf, 33 pages.

Michal Czubenko et al., (2015) Autonomous Driver based on an Intelligent System of Decision-making in Cognitive Computations Oct. 2015 vol. 7, Issue 5, downloaded from: https://link.springer.com/article/10.1007/s12559-015-9320-5, pp. 569-581.

Clifford Nass et al (2005) Improving Automotive Safety by Pairing Driver Emotion and Car Voice Emotion in CHI 205, 4 pages.

Mok et al (2015) Understanding Driver—Automated Vehicle Interactions Through Wizard of Oz Design Improvisation Proceedings of the Eighth International Driving Symposium on Human Factors in Driver Assessment, Training and Vehicle Design.

Adam Waytz et al. (2014), The mind in the machine: Anthropomorphism increases trust in an autonomous vehicle. Journal of Experimental Social Psychology.

M Sheller (2004) Automotive Emotions: Feeling the Car in—Theory, culture & society, Sage Journals, vol. 1 Issue 4-5.

Eyben, F., Wöllmer, M., Poitschke, T., Schuller, B., Blaschke, C. ,Färber, B. and Nguyen-Thien, N. Emtion on the Road—Necessity, Acceptance, and Feasibility of Affective Computing in the Car. Advances in Human-Computer Interaction vol. 2010 (2010), Article ID 263593.

International Patent Application No. PCT/US2019/014229 "International Search Report and Written Opinion" dated May 2, 2019, 12 pages.

International Patent Application No. PCT/US2019/014229 "International Search Report and Written Opinion" dated Oct. 15, 2020, 8 pages.

* cited by examiner

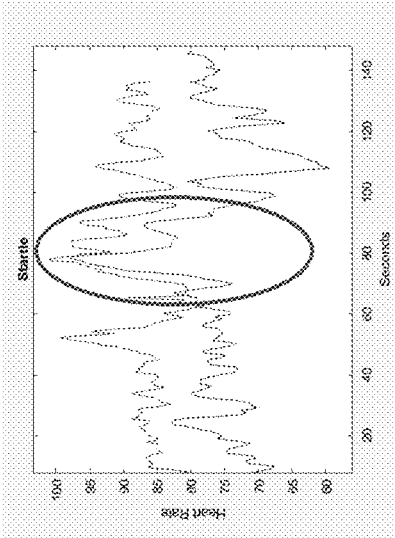
FIG. 1B
FIG. 1C
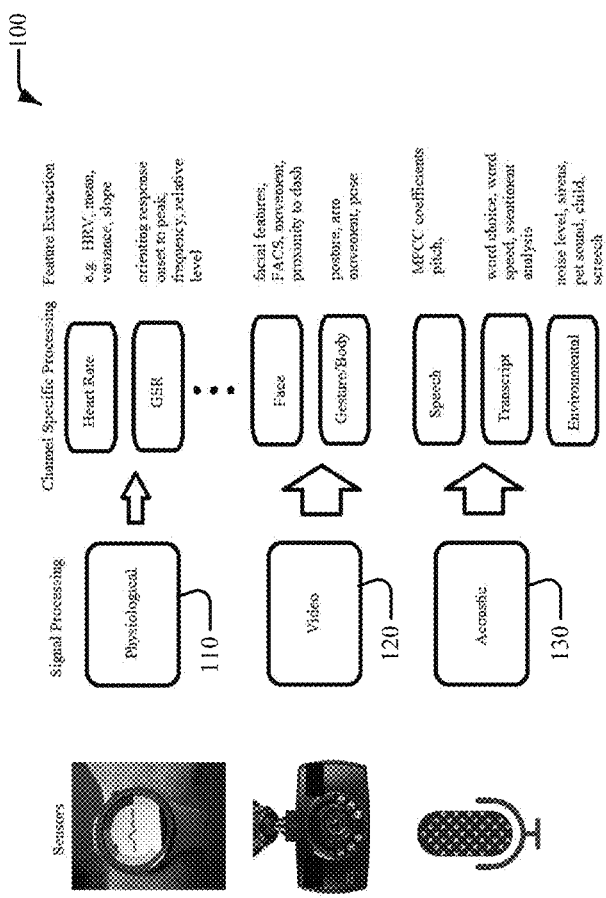
FIG. 1A

EMOTIONAL ADAPTIVE DRIVING POLICIES FOR AUTOMATED DRIVING VEHICLES

FIELD

The present disclosure generally relates to the field of electronics. More particularly, an embodiment relates to automotive systems and autonomous and/or machine assisted driving.

BACKGROUND

One fundamental limitation of existing automated vehicle systems is that they lack a proper monitoring and understanding of a person's reactions to the vehicle's operational decisions. Among other issues, the autonomous driving industry faces the challenge of establishing and maintaining trust between vehicle occupants and the artificial intelligence systems which control the vehicle. One fundamental problem in acceptance of autonomous driving systems is that a trust disconnect exists between passengers in a vehicle. Many people fully trust the vehicle's automated driving capabilities to the point of overconfidence (beyond the system limitations), while others may not trust the system under any condition. Accordingly, systems and methods to incorporate the emotional state of one or more passengers into the decision making process of an autonomous driving system may find utility.

BRIEF DESCRIPTION OF THE DRAWINGS

The detailed description is provided with reference to the accompanying figures. In the figures, the left-most digit(s) of a reference number identifies the figure in which the reference number first appears. The use of the same reference numbers in different figures indicates similar or identical items.

FIG. 1A is a diagram of illustrating elements of a system capable to implement emotional adaptive policies for automated driving vehicles in accordance with some examples.

FIGS. 1B, 1C, 1D, and 1E are diagrams illustrating emotional responses to various stimuli in accordance with some examples.

DETAILED DESCRIPTION

Figure 1D:
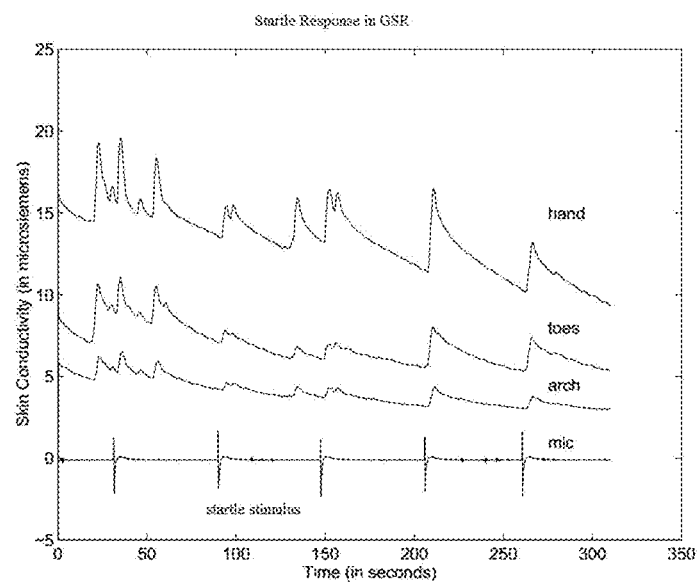
Figure 1E:
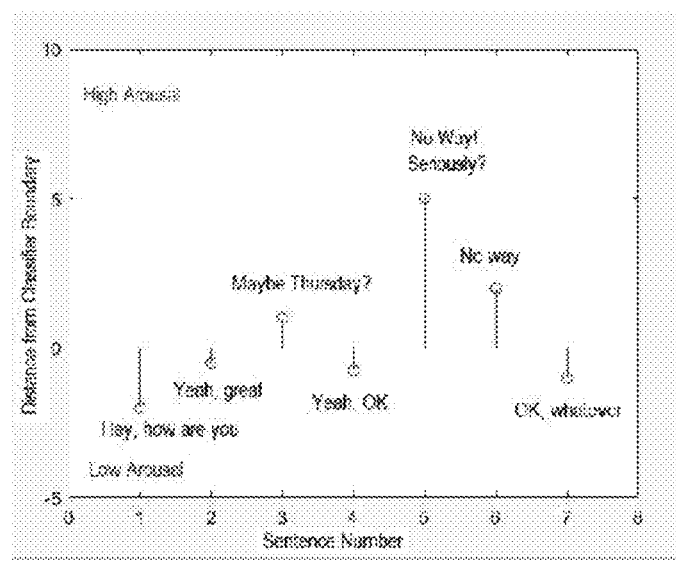

In the following description, numerous specific details are set forth in order to provide a thorough understanding of various embodiments. However, various embodiments may be practiced without the specific details. In other instances, well-known methods, procedures, components, and circuits have not been described in detail so as not to obscure the particular embodiments. Further, various aspects of embodiments may be performed using various means, such as integrated semiconductor circuits ("hardware"), computer-readable instructions organized into one or more programs ("software"), or some combination of hardware and software. For the purposes of this disclosure reference to "logic" shall mean either hardware, software, firmware, or some combination thereof.

As described above, one fundamental limitation of existing automated vehicle systems is that they lack a proper monitoring and understanding of a person's reactions to the vehicle's operational decisions. Subject matter described herein endeavors to apply emotion understanding to fulfill the limitations of the above mentioned efforts directed to providing an emotional aware autonomous system that takes into consideration the impacts that various autonomous driving decisions may have on the emotional comfort of passengers and has mechanisms to learn and incorporate those reactions safety and security goals to match passengers expectations and reactions.

In various aspects, subject matter described herein provides techniques to measure, monitor and model passengers' emotional state and mechanisms to adjust various driving policies of an automated vehicle to accommodate passengers' comfort based at least in part on real-time input on a passengers' emotional state-model. Various techniques are described to use a multimodal approach to estimate the emotional state of passengers in a vehicle. Measurements of passengers' emotional state may be integrated into an autonomous driving system operational mechanism. Also described are various examples of driving policy mechanisms, a rule based driving policy and an artificial intelligence based driving policy using reinforcement learning. The integration concepts described herein can be expanded to other autonomous system designs.

Referring to FIG. 1A, in some examples a multi-modal affective understanding system 100 may comprise a physiological channel 110, a video channel 120, and an acoustic channel 130. The system 100 gathers analytics for one or more passengers in an autonomous vehicle and tracks both individual reactions and reactions between persons in the vehicle. The system 100 may comprise wrist worn and chest worn heart-rate sensors, and real-time audio and video capture through multiple sources. Each channel captures and processes information and the information from the channels can be combined at both feature level and output level for effective classification. Various attributes of the channels 110, 120, 130 are described herein, but it will be understood that this is not an exhaustive list of sensors that could be used. A more expansive list encompasses any physiological sensor that could add evidence to affective state including for example: EMG, EEG, blood pressure, cortisol, respiration, or any physical perturbation measured by the vehicle itself such as balance, body pressure, grip pressure on steering wheel or armrest or any handle or grip, speed and force of acceleration or braking (in level 4 autonomous vehicle), etc. Information from any acoustic or any spectrum (infra-red to ultra violet and beyond) light sensor could also be incorporated.

In the system 100 the various sensors may be time-synchronized to collect information in the cabin of the vehicle. In one example physiological sensors may be worn by the passengers and may be are synchronized to a phone that is, in turn, wirelessly synchronized to an autonomous driving system for the vehicle. In another example the various sensors may establish a direct communication connection with the autonomous driving system for the vehicle.

Referring to FIGS. 1B and 1C, in some examples the system looks for signs of frustration and startle in our participants, both individually and collectively. FIG. 1B is a graph illustrating levels of frustration based upon, for example, aspects of a relative change in heart rate over a longer period of a drive in the vehicle. An example of a singular person's physiological signal analyzed in isolation indicating an increase in arousal/activation level, an indicator of frustration or stress. Referring to FIG. 1C, Startle and frustration indicators can also be found across many other physiological channels, for example galvanic skin response (GSR).

Referring to FIG. 1D, there is presented an example of GSR a multi-passenger fused signal indicator of startle. As indicated in FIG. 1D a GSR startle response presents as a sharp increase after a prime. In this case the prime shown is a microphone burst of sound labeled "mic" and the response is shown at three sensed locations, across the hand and across the feet from both the toes and the arch of the foot. It is more likely that an emotionally impactful driving event occurred if multiple passengers exhibit simultaneous startle responses.

An indication of a passenger's emotional state can also be detected from the acoustic properties of the passenger's voice, for example the relative loudness, changes in pitch, speed of speech, etc. In some examples multiple voice features may be used to quantify vocal properties, e.g., energy, $F_0$, or mel-frequency (MFCC) Coefficients. In one example the SVM classifier may use these features to recognize high and low arousal acoustic properties to infer how "excited" the speech is, for example is the person a little angry or very angry.

In some examples the system may comprise a Sentiment parameter. In addition to the information that can be quantified from the acoustic signal of speech, the system may also extract the content of speech (i.e., words said). For example, if the system recognizes expletives or a passenger saying to the car "Stupid car, you almost hit that post!" the system can infer negative sentiment in the expression. Conversely, if two people are having a pleasant conversation such as "I am really excited about going to Italy. We went last year and it was great!" the system can infer positive sentiment. Sentiment may be used to discriminate between, for example, happy excited speech and an angry excited speech.

In some examples the system combines emotional channel information at to create a holistic prediction of a passenger's emotional state, and attempt to infer if the emotional reaction is in response to a driving related situation and in particular to an action taken by the car. The system can then build a state model of emotional states.

The output of the passenger state emotional classifier can have multiple dimensions. In some examples the system utilizes a minimum of four, namely, emotional state classification $\in$ {startle, stressed, frustrated, . . . }, a confidence value $\in [0, 1]$ emotional state valence $\in [-1, 1]$, sentiment $\in [-1,1]$ and arousal $\in [0,1]$. This passenger state vector is provided as input for the driving policy engine.

Figure 2A:
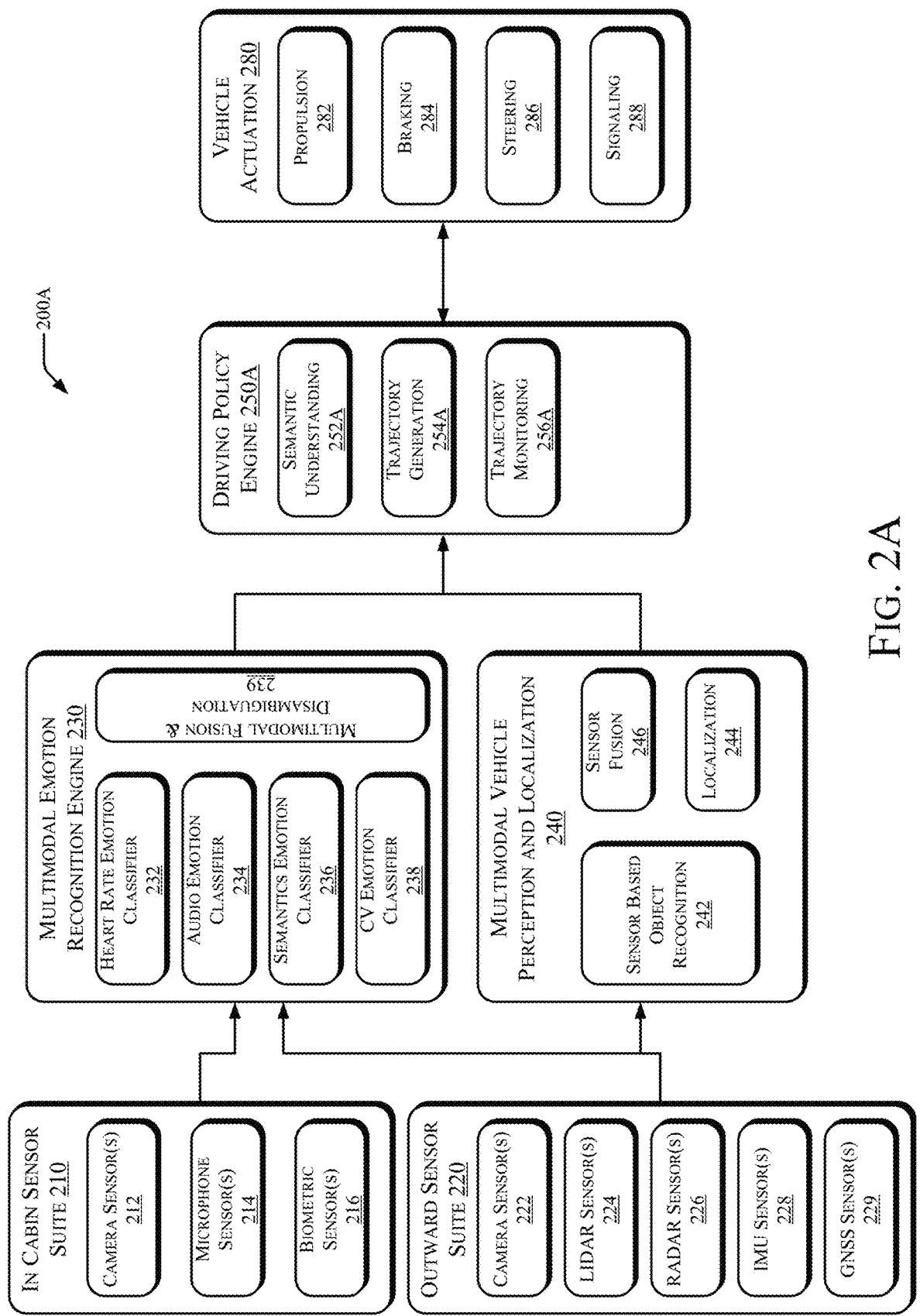
FIGS. 2A, 2B, and 2C are schematic illustrations of systems capable to implement emotional adaptive policies for automated driving vehicles in accordance with some examples.
Figure 2B:
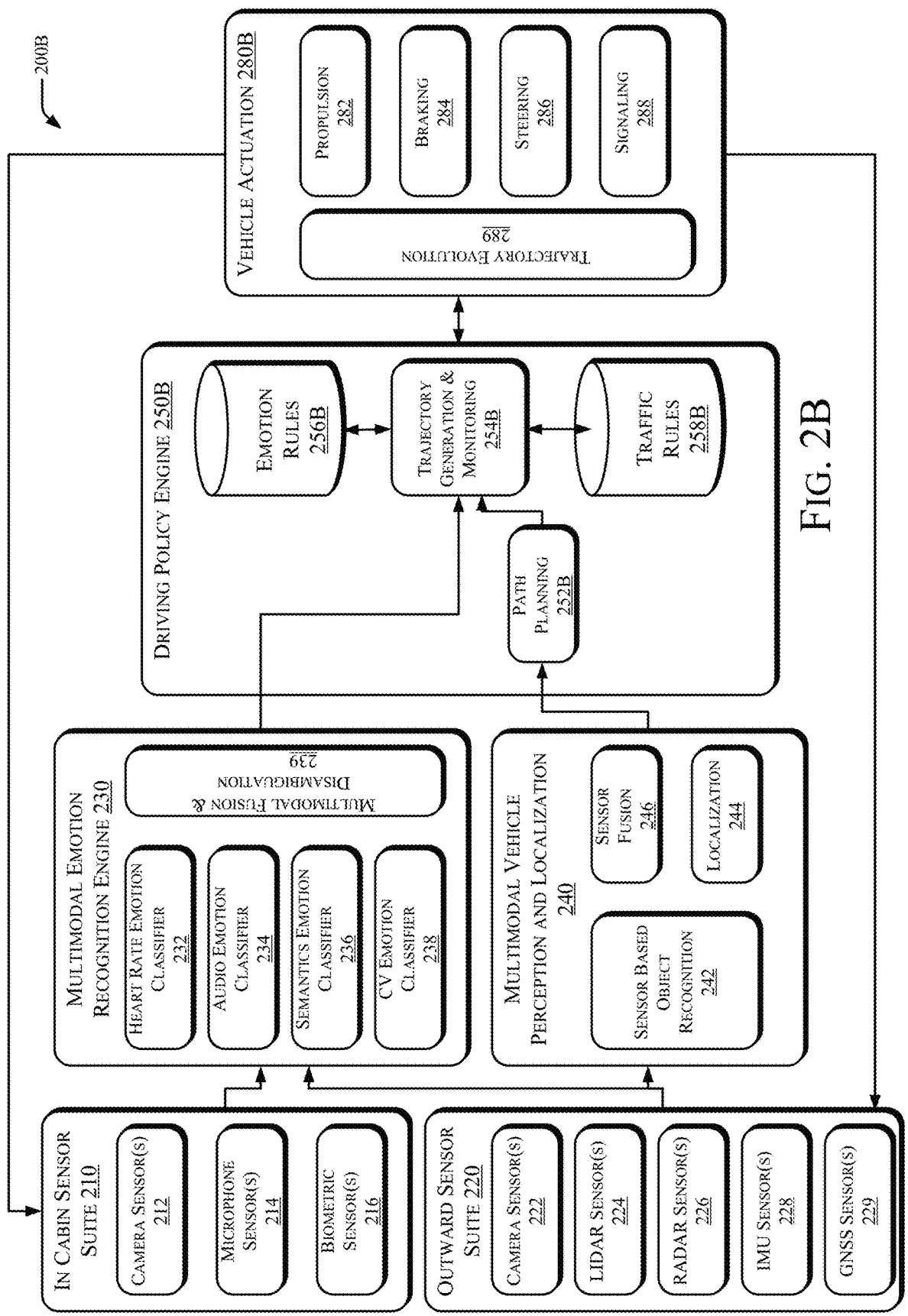
Figure 2C:
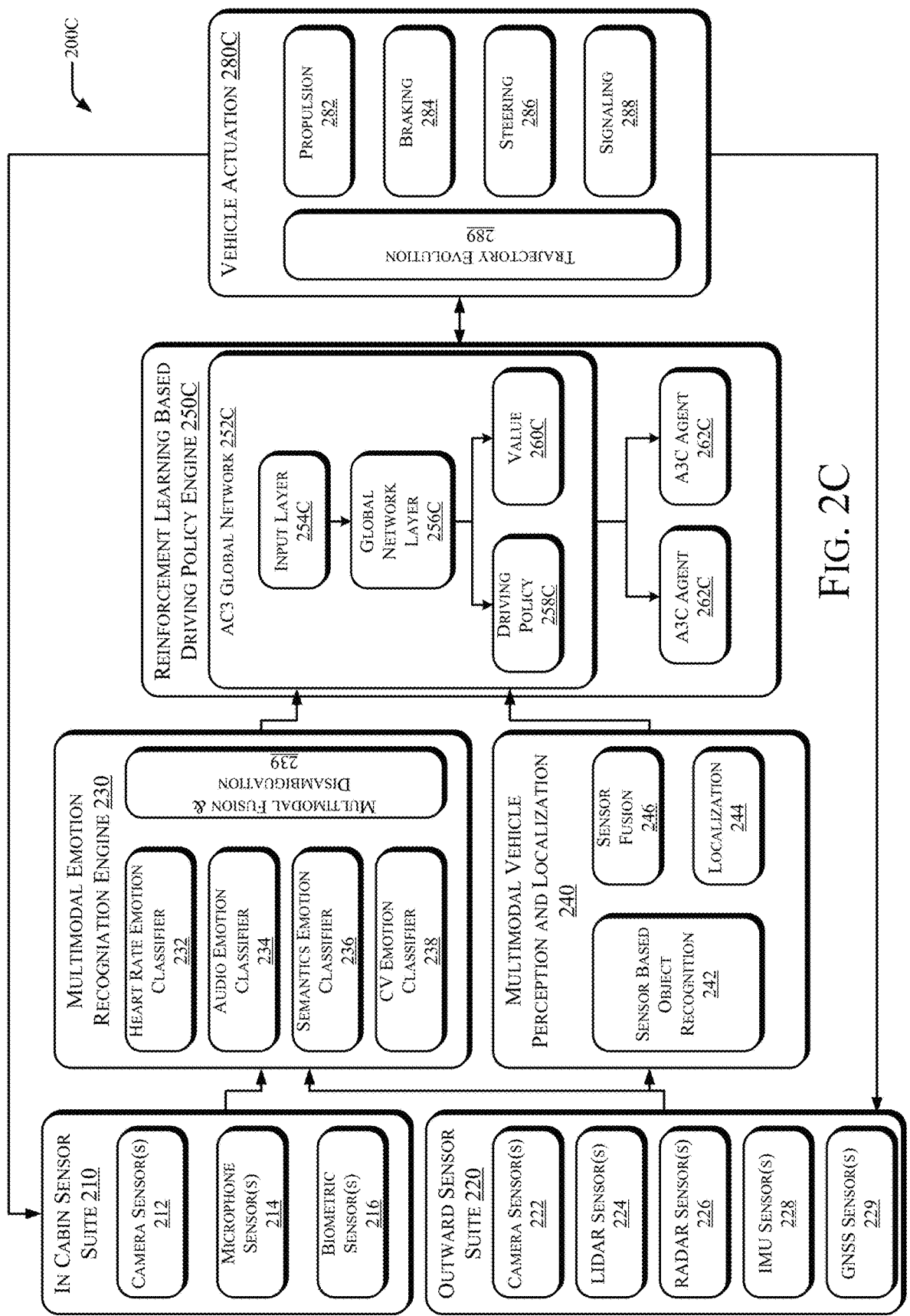

FIGS. 2A, 2B, and 2C are schematic illustrations of systems capable to implement emotional adaptive policies for automated driving vehicles in accordance with some examples. Referring first to FIG. 2A in one example a system 200A comprises an in-cabin sensor suite 210 which may comprise one or more camera sensor(s) 212, one or more microphone sensors 214 and one or more biometric sensors 216, as described above. Camera sensor(s) 212 may monitor visual aspects of the in-cabin environment. Microphone sensor(s) 214 may monitor auditory aspects of the in-cabin environment. Biometric sensor(s) 216 may gather biometric data from one or more passengers in the vehicle.

System 200A may further comprise an outward sensor suite 220 which may comprise one or more camera sensors 222, one or more LIDAR sensors 224, one or more RADAR sensors 226, one or more inertial monitoring unit (IMU) sensors 228 and one or more global navigational satellite system (GNSS) sensors 229. Camera sensors(s) 222, RADAR sensor(s) 224, and LIDAR sensor(s) 226 may monitor one or more aspects of the external environment. IMU sensor(s) may track movement of the vehicle using inertial measurements. GNSS sensor(s) 229 may monitor a location of the vehicle using one or more satellite-based location systems.

System 200A may further comprise a multimodal emotion recognition engine 230 which may comprise a heart rate emotion classifier 232, an audio emotion classifier 234, a semantics emotion classifier 236, a computer vision (CV) emotion classifier 238, and a multimodal fusion and disambiguation module 239. The multimodal emotion recognition engine 230 receives as inputs the outputs of the various sensors in the in-cabin sensor suite 210 and the outward sensor suite 220. The heart rate emotion classifier 232 may receive inputs from one or more biometric sensor(s) monitoring the heart rate of passengers in the vehicle and may apply heuristics to the heart rate inputs to assess an emotional state of the passengers. Audio emotion classifier 234 may receive inputs from one or more microphone sensor(s) 214 and may apply heuristics to the heart rate inputs to assess an emotional state of the passengers. Semantics emotion classifier 236 may receive inputs from one or more microphone sensor(s) 214, process the inputs to ascertain semantics of the audio input (e.g., using a voice recognition system) as described above, and may apply heuristics to the heart rate inputs to assess an emotional state of the passenger(s). CV emotion classifier 238 may receive inputs from one or more camera sensor(s) 214 and process the inputs to ascertain an emotional state of the passenger(s). Multimodal fusion and disambiguation module 239 may combine the outputs of one or more of the classifier modules to generate a multimodal estimate of the emotional state of one or more passenger(s) in the vehicle.

System 200A may comprise a multimodal vehicle perception and localization module 240, which may comprise a sensor based object recognition module 242, a sensor fusion module 244, and a localization module 246. Sensor based object recognition module 242 may receive inputs from one or more camera sensor(s) 214 and process the inputs to recognize one or more objects in the environment surrounding the vehicle. Localization module 244 may receive inputs from one or more of the IMU sensor(s) and/or GNSS sensor(s) and may determine a location of the vehicle. Sensor fusion module 246 may combine the combine the outputs of the sensor based object recognition module and the localization module to generate a location and context state of the vehicle.

System 200A may comprise a driving policy engine 250A, which may comprise a semantic understanding module 252A, a trajectory generation module 254A, and a trajectory monitoring module 256A. The semantic understanding module 252A may receive inputs from the audio emotion classifier and/or the semantics emotion classifier. Trajectory generation module 254A may receive inputs from one or more of the sensors in the in-cabin sensor suite 210, one or more of the sensors in the outward sensor suite 220, the multimodal emotion recognition engine 230, and the multimodal vehicle perception and localization module 240 and may generate a trajectory for the vehicle. Trajectory monitoring module 256A may receive inputs from one or more of the sensors in the outward sensor suite 220 (e.g., the IMU sensor(s) and/or the GNSS sensor(s) 229) to monitor the trajectory of the vehicle as well as from the vehicle actuation system 280.

System 200A may comprise a vehicle actuation module 280, which may comprise a propulsion module 282, a braking module 284, a steering module 286, and a signaling module 288. Propulsion module 282 may receive inputs from one or more of the sensors in the in-cabin sensor suite 210, one or more of the sensors in the outward sensor suite 220, and the driving policy engine 250A and adjusts the propulsion of the vehicle. Braking module 284 may receive inputs from one or more of the sensors in the in-cabin sensor suite 210, one or more of the sensors in the outward sensor suite 220, and the driving policy engine 250A and adjusts the braking of the vehicle. Steering module 286 may receive inputs from one or more of the sensors in the in-cabin sensor suite 210, one or more of the sensors in the outward sensor suite 220, and the driving policy engine 250A and adjusts the steering of the vehicle. Signaling module 288 may receive inputs from one or more of the sensors in the in-cabin sensor suite 210, one or more of the sensors in the outward sensor suite 220, and the driving policy engine 250A and adjusts the signaling of the vehicle.

Thus, the system 200 depicted in FIG. 2A comprises both internal and external multimodal sensors which may be used by the emotion recognition engine and vehicle perception and localization modules to produce the car state and passenger states which are fed into the driving policy engine, which outputs the sequence of states (trajectory) to the low level controller that actuates the vehicle.

In an automated vehicle, the driving policy system is responsible to evaluate the current state of the vehicle, the possible actions to be applied to achieve a goal and to determine the optimal control guidelines. In general, driving policies take into consideration a set of environment observations and car states and a set of actions to be applied. The system 200 depicted in FIG. 2A expands the environment observation by providing in-vehicle environment in addition to exterior environment and passenger state in addition to car state.

Another example of a system capable to implement emotional adaptive policies for automated driving vehicles is depicted in FIG. 2B. Referring to FIG. 2B, in some example the system 200B comprises an in-cabin sensor suite 210, an outward sensor suite 220, a multimodal emotion recognition engine 230, and a multimodal vehicle perception and localization module 240 that are substantially the same as those described with reference to FIG. 2A. Therefore, in the interest of clarity and brevity the descriptions of these modules will not be repeated.

System 200B may comprise a driving policy engine 250B, which differs in structure from the driving policy engine 250A described with reference to FIG. 2A. Driving policy engine 250B may comprise a path module 252B, a trajectory generation and monitoring module 254B, and data stores comprising emotion rules 256B and traffic rules 258B. The path planning module 252A may receive inputs from multimodal vehicle perception and localization module 240 to determine a path for the vehicle to follow. Trajectory generation and monitoring module 254B may receive inputs from one or more of the sensors in the in-cabin sensor suite 210, one or more of the sensors in the outward sensor suite 220, the multimodal emotion recognition engine 230, and the multimodal vehicle perception and localization module 240, the data store comprising emotion rules 256B, and the data store comprising traffic rules 258B and may generate and monitor a trajectory for the vehicle.

System 200B may comprise a vehicle actuation module 280B, which may comprise a propulsion module 282, a braking module 284, a steering module 286, and a signaling module 288 that are substantially the same as those described with reference to FIG. 2A. Therefore, in the interest of clarity and brevity the descriptions of these modules will not be repeated.

Vehicle actuation module 280B may comprise a trajectory evolution module 289 which may receive inputs from one or more of the sensors in the in-cabin sensor suite 210, one or more of the sensors in the outward sensor suite 220, and the trajectory generation and monitoring module 254B and adjusts the trajectory of the vehicle.

The traffic rules module 258B may comprise knowledge base system containing traffic regulations, such as maximum speed allowed on the road segment and right of way behavior. The emotion rules module 256 may also comprise a knowledge base system containing emotional states mappings, e.g. reduce acceleration delta when passenger is startled or increase speed if user is frustrated and speed is low. Most of those rules can be define as inferences of the type IF (X) THEN (Y).

The trajectory generation and monitoring module 254B works thus as an inference engine. The module 254B performs searches on both knowledge bases, match the appropriate rules based on car and passenger states, filters them and composes the trajectory plan which includes the path planning and the dynamic execution values. The path planning result is fitted to the traffic rules and to account for emotional responses of the passengers and optimize the vehicle kinematic constraints for comfort.

Figure 3:
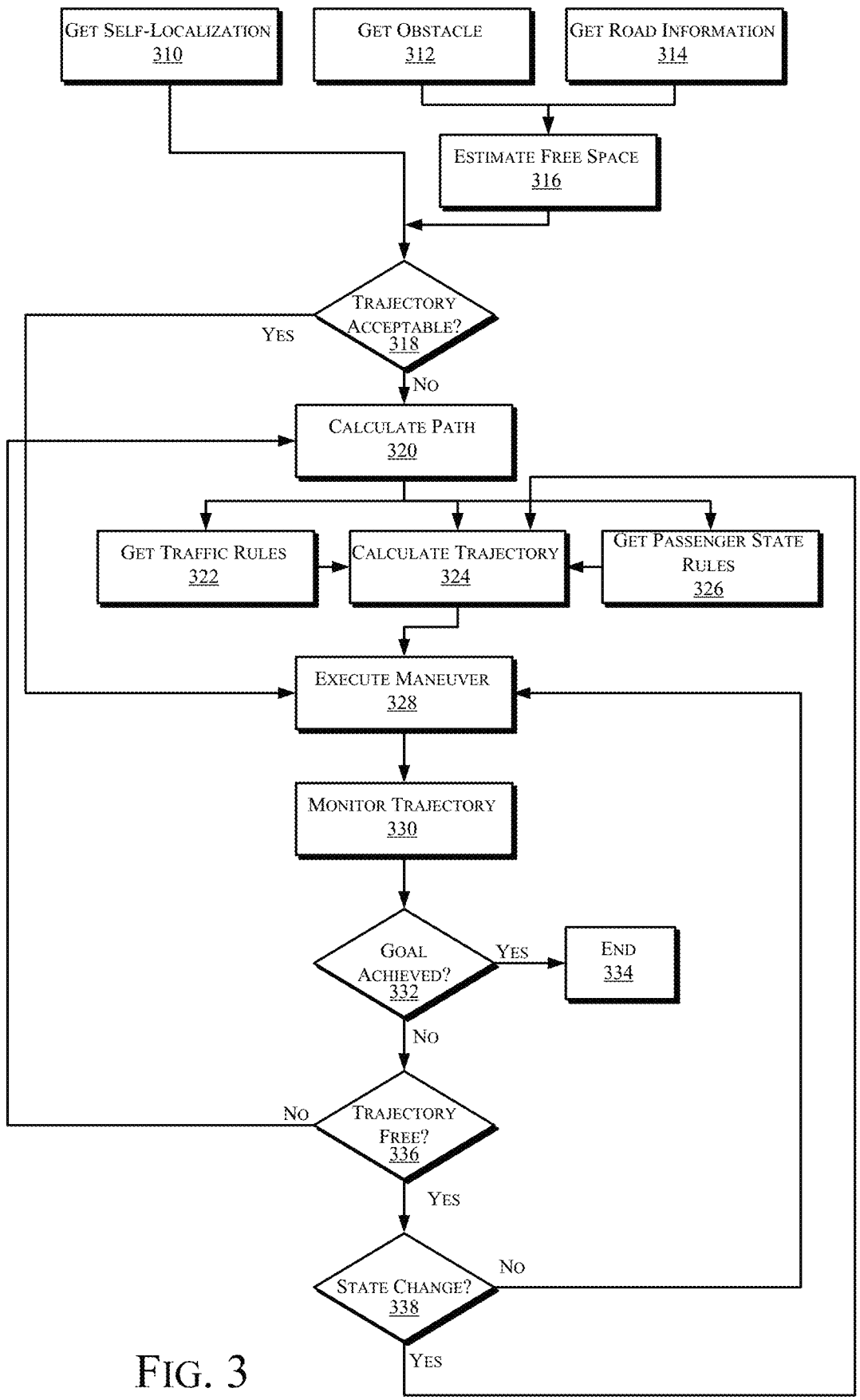
FIG. 3 is a flow diagram illustrating operations in a method to implement emotional adaptive policies for automated driving vehicles in accordance with some examples.

FIG. 3 is a flow diagram illustrating operations in a method to implement emotional adaptive policies for automated driving vehicles in accordance with some examples. In some examples the operations depicted in FIG. 3 may be implemented by components of the driving policy engine 250A or the driving policy engine 250B, alone or in combination with other components of the systems 200A, 200B depicted in FIGS. 2A-2B.

Referring to FIG. 3, at operation 310 localization data is retrieved, e.g., from localization module 244. At operation 312 information about one or more obstacles is retrieved, e.g., from sensor based object recognition module 242. At operation 314 information about the road(s) on which the vehicle is traveling, e.g., from the various sensors in the outward sensor suite 220 alone or in combination with external sources, e.g., mapping resources.

At operation 316 an amount of free space surrounding the vehicle is estimated based on the obstacle information and the road information. At operation 318 it is determined whether the current trajectory is acceptable. If, at operation 318 the current trajectory is not acceptable then control passes to operations and traffic rules are obtained, e.g., from the traffic rules data store 258B. Contemporaneously, at operation 326, passenger state rules are obtained, e.g., from emotion rules data store 256B. At operation 324 a trajectory is calculated (e.g., in the trajectory generation module 254A or the trajectory generation and monitoring module 254B) using the path input from operation 320, the traffic rules from operation 322, and the passenger rules from operation 326.

The trajectory generated in operation may be passed At operation 328 the trajectory determined in operation 324 is used to execute one or more maneuvers for the vehicle. For example, the trajectory may be passed to the vehicle actuation module 280A or 280B, which in turn may activate one or more actuators to complete the maneuver.

At operation 330 the trajectory of the vehicle is monitored (e.g., in the trajectory monitoring module 256A or the trajectory generation and monitoring module 254B). If, at operation 332 the goal of the maneuver is achieved then control passes to operation 334 and the maneuver ends. By contrast, if at operation 332 the goal is not achieved then control passes to operation 336, where it is determined whether the trajectory is free. If the trajectory is no free, then control passes back to operation 318. By contrast, if at operation 336 the trajectory is free then control passes to operation 338, where it is determined whether there has been a change in a passenger's emotional state.

If, at operation 338 there is no change in the passenger's emotional state then control passes back to operation 328 and the maneuver continues to execute. By contrast, if at operation 338 there is a change in the passenger's emotional state then control passes to operation 324 and a new trajectory is calculated as described above.

Thus, operations 318-338 define a loop pursuant to which the trajectory of a vehicle may be modified and monitored based on a number of inputs including, but not limited to, inputs pertaining to the emotional state of passengers.

Formally this system can be expressed as follows: The vehicle is assumed to operate in a workspace $W \epsilon^{R2}$ At a particular point in time and space, this workspace surrounding the vehicle contains a number of obstacles (vehicles)/limitations (lane markings), being $wo_i$, the "ith" of such obstacles/limitations. Thus the drivable space (workspace free of obstacles) is defined as $w_{\perp}free = w - U(\lceil wo \rceil_i)$.

The path planning problem is presented by a tuple consisting of an initial point $X_{init}$, an end point, $X_{goal}$ and the drivable space between those points $w_{free}$. Path planning is defined as process $\varphi$ in which given a function $\delta:[0,T] \rightarrow w$, where the initial point $\delta(0)=X_{init}$ and the final point $\delta(T)=X_{goal}$, path planning $\varphi$ is a continuous process where $\delta(t) \in w_{free}$. Thus we derive a formal definition of path:

$$\{(t,\delta(t)) - \lnot | 0 \leq t \leq T, \delta(0) = X_{\perp}init, \delta(T) = X_{\perp}goal\} = p_{\perp}$$
$$(0 \rightarrow T) \in P.$$

Since there can be multiple paths in the free space communicating the starting and end points so we define optimal path planning through a cost function $C:P \rightarrow N_o$ where P denotes the set of all possible paths. Optimal path planning is defined as a process $\varphi'$ that uses the previous cost function to restrict the solution to the optimal solution $\delta'$ so that $C(p')=\min(C(P))$. The main parameter to the cost function is usually shortest path as it saves fuel/energy but other parameters can be added to optimize route to specific parameters.

The trajectory planning applies kinematic constrains to $\varphi'$ in a combination of polynomials that transverses time $\dot{x}(t)=f(x(t),u(t))$. Where x(t) determines the vehicle evolving state across the path and u(t) determines the control parameters applied across time. The control parameters for a driving vehicle can be reduced to 2 Degrees Of Freedom (DOF) to control lateral and longitudinal deviations of the vehicle through input on steering wheel angle AO and velocity $\Delta v$ (as result of break/gas pedal inputs). In the driving policy the output is impacted by 3 components, the output to the next way point in the path plan (G), the output constraints given by the emotional state (E) and the output constraints given by traffic rules (R):

$$u(t) = \frac{1}{\Delta T} \int_{t-\Delta T}^{t} k_g G(s) + k_e E(s) + k_r R(s) ds$$

where $\Delta T$ is a scalar for the time window in which the output will be applied, $k_g$, $k_e$, and $k_r$ are weights following the condition $(k_{\perp}g+k_{\perp}e+k_{\perp}r=1)$. In the time windows where emotional state is neutral $k_e=0$ and respectively will remain null when there is no transgression of traffic rules (e.g. speed limit). In any other cases, E(s) and R(s) will apply the corrective deltas on $\Delta\theta$ and $\Delta v$ until the vehicle and passenger states are back within optimal parameter range.

The implementation of the vehicle controller can follow Mixed-Integer Linear Programming (MILP) or Proportional Integral-Derivative (PID) methods with the parametric additions described above. The system can also be expanded with increasing degrees of freedom based on other control parameters to perform complex maneuvers in time and 3D space.

Reinforcement Learning Emotional-Aware Driving Policy

Another implementation of driving policies can follow bioinspired algorithms which originate from mimicking biological behaviors to solve the path planning and trajectory planning. Those can be divided into evolutionary algorithms that use stochastic search approaches imitating natural evolution and social behavior (i.e. genetic algorithms, ant colony optimization and particle swarm optimization) and neural network algorithms that mimic the behavior of the brain. The neural network approach has received particular interest in the robotics and autonomous driving community in particular with the successful application of deep learning techniques to the perception-decision-actuation pipeline. Within deep learning there are multiple approaches such as Supervised Learning, where the driving policy is directly presented a sequence of independent examples of correct predictions to make in different circumstances, Imitation Learning, where the driving policy is provided demonstrations of actions of a good strategy to follow in given situations and Reinforcement Learning (RL), where the driving policy explores the space of possible strategies and receives feedback on the outcome of the choices made to deduce a "good"—or ideally optimal—policy (i.e., strategy or controller).

Described herein are examples of a system that continuously adapts to a particular passenger's emotional state using a reinforcement learning based driving policy system enhanced with emotional-state awareness. Among the different algorithms available in RL, an implementation using Asynchronous Actor Advantage Actor Critic (A3C) is described herein. The system is described at a high-level in FIG. 2C.

Referring to FIG. 2C, in some example the system 200C comprises an in-cabin sensor suite 210, an outward sensor suite 220, a multimodal emotion recognition engine 230, and a multimodal vehicle perception and localization module 240 that are substantially the same as those described with reference to FIG. 2A. Therefore, in the interest of clarity and brevity the descriptions of these modules will not be repeated.

System 200C may comprise a reinforcement learning (RL) based driving policy engine 250C, which differs in structure from the driving policy engine 250A described with reference to FIG. 2A. Driving policy engine 250C may comprise AC3 global network 252C, which in turn comprises an input layer 254C, a global network layer 256C, a driving policy layer 258C, values 260C, and one or more AC3 Agents 262C.

In this implementation the RL-based driving policy engine 250C receives as input the car state and passenger states. The A3C Global Network 252C copies this input to the individual A3C agents 262C running multithreaded in available processor cores where number of agents can be N−1 number of cores of the system. Each agent 262C experiences the environmental input and produces a value and policy loss results that gets aggregated (learned) into the A3C Global network 252C, which will then produce the final outcome in the form of the optimal driving policy action. This trajectory is passed on to the vehicle actuation for execution.

System 200C may comprise a vehicle actuation module 280B, which may comprise a propulsion module 282, a braking module 284, a steering module 286, and a signaling module 288 that are substantially the same as those described with reference to FIG. 2A. Therefore, in the interest of clarity and brevity the descriptions of these modules will not be repeated.

Vehicle actuation module 280C may comprise a trajectory evolution module 289 which may receive inputs from one or more of the sensors in the in-cabin sensor suite 210, one or more of the sensors in the outward sensor suite 220, and the RL-based driving policy engine 250C and adjusts the trajectory of the vehicle.

Figure 4:
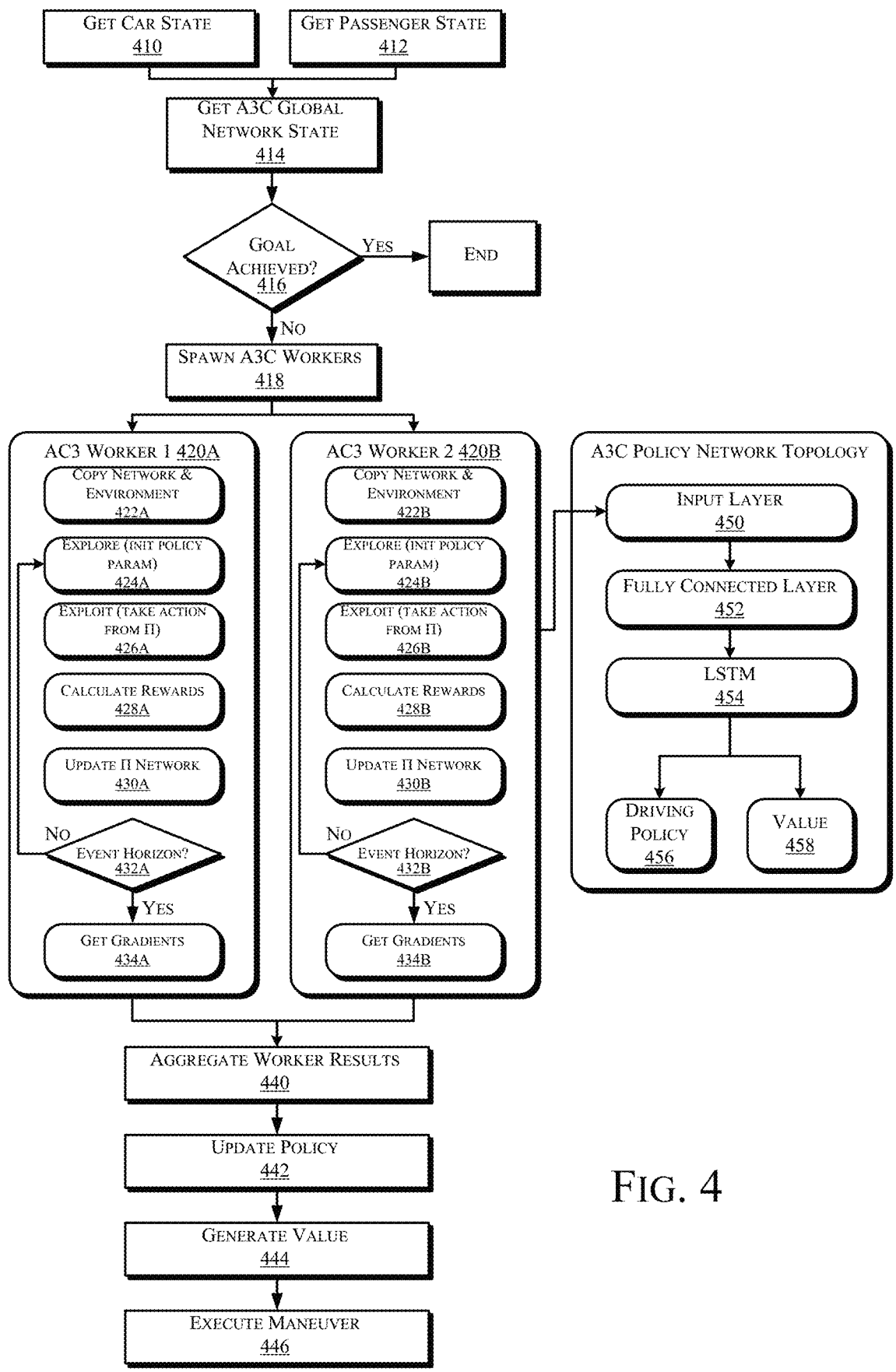
FIG. 4 is a flow diagram illustrating operations in a method to implement emotional adaptive policies for automated driving vehicles in accordance with some examples.

One example of the decision making and adaptive learning process on the RL-based driving policy engine is detailed in the diagram flow in FIG. 4. Referring to FIG. 4, the driving policy engine 250C gets car state information (operation 410) and passenger(s) state information (operation 412) including environmental states and initializes (operation 414) the A3C Global network parameters which include shared parameter vectors and event horizon (i.e., how far ahead is the vehicle planning the impact of the actions). If, at operation 416, the driving policy considers that the vehicle has not completed the driving policy maneuver, the A3C Global Network agent 262C then spawns (operation 418) A3C workers in a multithreaded fashion according to the available number of processing cores (N).

The environment input is copied to the individual A3C workers 420A, 420B, etc., which will initialize a policy network. In one example an A3C network topology may comprise an input layer 450, a fully connected layer 452, a long-short term memory (LSTM) module 454, driving policies 456 and values 458. In some examples this network establishes exploration parameters and takes the corresponding future action, measures expected reward(s) and updates the policy for as many actions as the event horizon specifies. At that point the AC3 worker 420A, 420B calculates the cumulative rewards: the value loss, policy loss and the entropy of the policy to obtain learning gradients (operation 434). The gradients of each worker 420A, 420B are passed to the global network that will update the network parameters having learned in parallel from all the workers 420A, 420B experience and perform the best global action (i.e., trajectory). This learning process allows for continuous updating in the computation of the best vehicle action in a function that maps vehicle state and passenger state to vehicle actuation and that is optimized over time for trajectory and passenger emotional state rewards.

At operation 440 the results of the A3C workers 420A, 420B are aggregated and at operation 442 a policy is updated and a value generated (operation 444), and at operation 446 the maneuver is executed.

Functionally the system is expressed as follows. Given a car-passenger state s∈S and a driving action α∈A a function may be defined that maps the car-passenger states to the driving actions. This function may be referred to as a driving policy $\pi(s)=P(\alpha_1 t \mid s_1 t)$. At each time step t, the vehicle perceives a state $S_t$, and selects an action at from a set of possible actions A according to policy π. In return, the agent receives the next state $S_{t+1}$ and a scalar reward $\gamma_t$. The process continues until the vehicle reaches the final state or the event Horizon H (i.e., the amount of time that policy looks into the future to calculate a cumulative reward).

The reward can be calculated as a weighted sum of terms: e.g. positively weighted speed ($v_t$ in km/h), distance traveled towards the goal ($d_t$ in km) and emotional state valence (eval$_t \in [-1,1]$), and negatively weighted distance to front object ($c_t$), overlap with left lane shoulder ($s_t \in [0,1]$), overlap with the opposite lane ($o_t \in [0,1]$) and emotional state arousal (earo$_t$):

$$r_t = k_{d_t}(d_{t-1} - d_t) + k_{v_t}(v_{t-1} - v_t) + k_{eval_t}(eval_{t-1} - eval_t)$$

$$k_{c_t}(ct_{t-1} - c_t) - k_{s_t}(s_{t-1} - s_t) - k_{o_t}(o_{t-1} - o_t) - k_{earo_t}(earo_{t-1} - earo_t)$$

Notice that the reward function could be more complex and further criteria could be added. The values of the coefficients k can also be changed to modify the learning preferences. We define the cumulative reward as:

$$R = \sum_{k=o}^{H} \gamma^t r_{t+k}$$

where γ is the discount factor across time steps h and ∈(0,1].

The goal of the driving policy engine is to find an optimized driving policy π* as the one that maximizes the expected return R. In our case this corresponds to the vehicle getting where it needs to go with the passenger experiencing a positive emotional experience. A3C is a policy searching algorithm so it directly parameterizes the policy $\pi(\alpha_1 t \mid s_1 t; \theta)$ and updates the parameters θ by performing gradient ascent on R and subtracting a learned baseline that corresponds to the return value from following policy π from state s. This subtraction is known in A3C as the advantage Ad of action $\alpha_t$ in state and can be expressed as:

$$Ad(\alpha_t;s_t)=Q(\alpha_t;s_t)-V(\alpha_t;s_t)$$

Because R is an estimate of $Q(\alpha_t; s_t)$ and the baseline is an estimate of $V(\alpha_t; s_t)$.

At the end of the event Horizon the algorithm computes the value loss $V_L$ as:

$$\Sigma Ad(\alpha_t;s_t)^2$$

and the policy loss as:

$$\pi_{\downarrow}L=-\log \mathbb{E}_{(\pi(t)A(t)-\beta H(t))}$$

with the last parameter being the Shannon Entropy (spread of action probabilities) and the parameter β that regulates the strength of the entropy regularization.

Following this process the algorithm updates the network using the information provided by the environment. With time the agent gets more and more accurate knowledge of the environment, based on which the agent's policy eventually converges to the optimal policy π*. A3C algorithm multithreads that experience creating parallel actors that can forecast future different actions and learn a cumulative experience from them.

The subject matter described herein is one example of applying reinforcement learning to build a continuously adapting driving policy to optimize control input to the emotional state or well-being of the driver. Other RL algorithms could be applied with similar results and other machine learning techniques could be applied for similar purpose such as imitation learning or supervised learning.

Figure 5A:
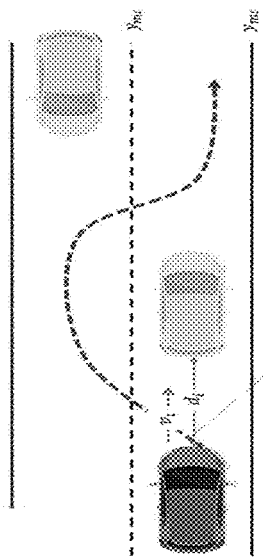
FIG. 5A, 5B, 5C and FIG. 5D are diagrams illustrating driving maneuvers in accordance with some examples.
Figure 5B:
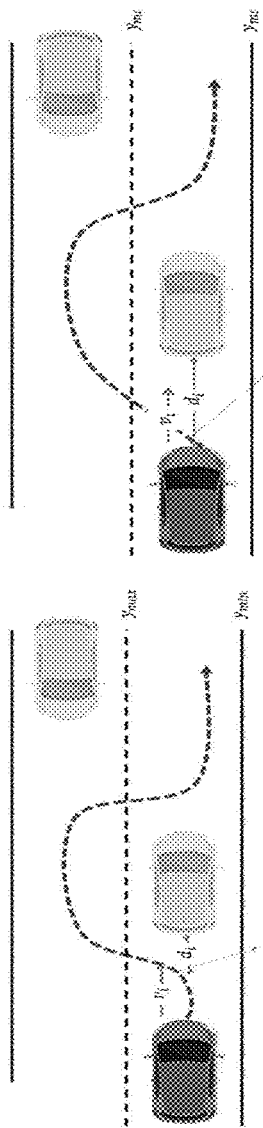
Figure 5C:
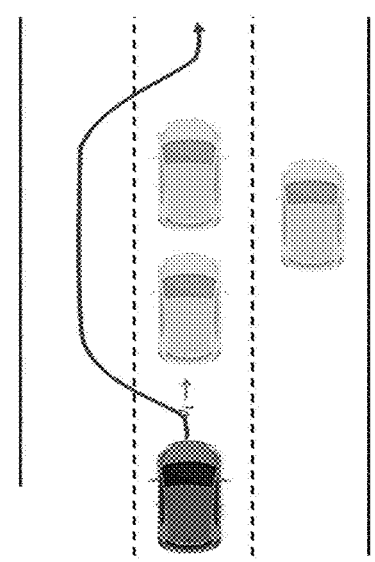
Figure 5D:
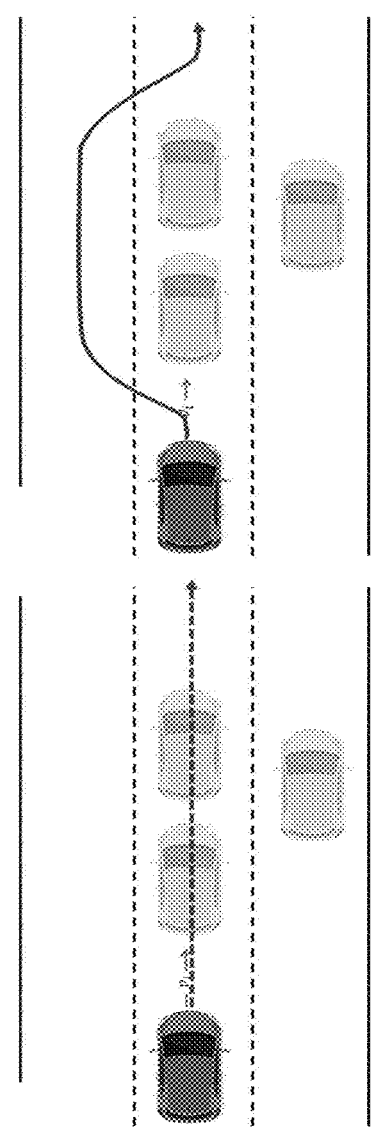

The previously described implementation can be applied during automated or cooperative driving environments to customize the vehicle response and behavior to road events. FIG. 5A, 5B, 5C and FIG. 5D are diagrams illustrating driving maneuvers in accordance with some examples. Referring to FIG. 5A illustrates a take-over situation in which short head distance (di) leads to stressed situation. FIG. 5B illustrates an optimized take over behavior based on emotional state with longer head distance and smoother lane changing FIG. 5C illustrates a simple lane following driving policy in urban scenarios. Due to low vehicle speed this scenario generates frustration. FIG. 5D illustrates an updated driving policy in which average speed is increased by allowing for multiple lane changes to overtake slower vehicles.

Figure 6:
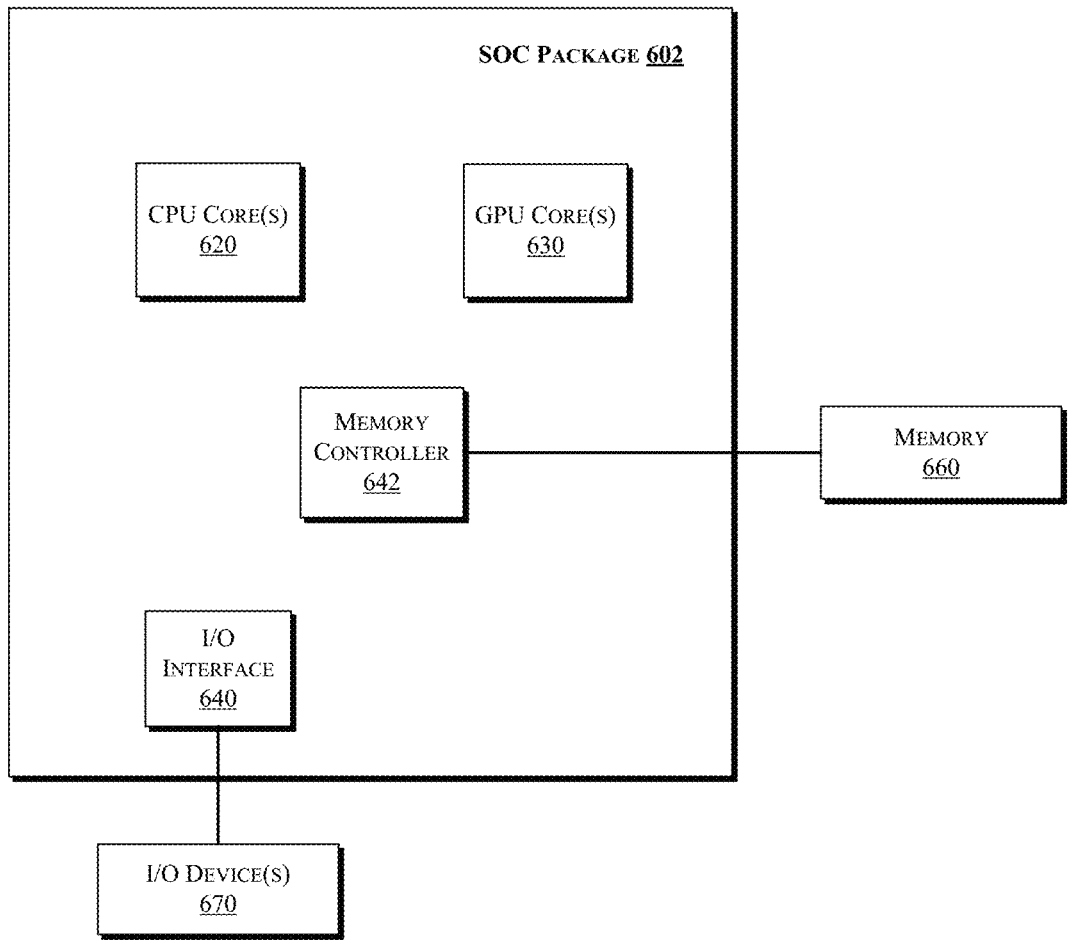
FIG. 6 illustrates a block diagram of a system on chip (SOC) package in accordance with an embodiment.

FIG. 6 illustrates a block diagram of a system on chip (SOC) package in accordance with an embodiment. As illustrated in FIG. 6, SOC 602 includes one or more Central Processing Unit (CPU) cores 620, one or more Graphics Processor Unit (GPU) cores 630, an Input/Output (I/O) interface 640, and a memory controller 642. Various components of the SOC package 602 may be coupled to an interconnect or bus such as discussed herein with reference to the other figures. Also, the SOC package 602 may include more or less components, such as those discussed herein with reference to the other figures. Further, each component of the SOC package 620 may include one or more other components, e.g., as discussed with reference to the other figures herein. In one embodiment, SOC package 602 (and its components) is provided on one or more Integrated Circuit (IC) die, e.g., which are packaged into a single semiconductor device.

As illustrated in FIG. 6, SOC package 602 is coupled to a memory 660 via the memory controller 642. In an embodiment, the memory 660 (or a portion of it) can be integrated on the SOC package 602.

The I/O interface 640 may be coupled to one or more I/O devices 670, e.g., via an interconnect and/or bus such as discussed herein with reference to other figures. I/O device(s) 670 may include one or more of a keyboard, a mouse, a touchpad, a display, an image/video capture device (such as a camera or camcorder/video recorder), a touch screen, a speaker, or the like.

Figure 7:
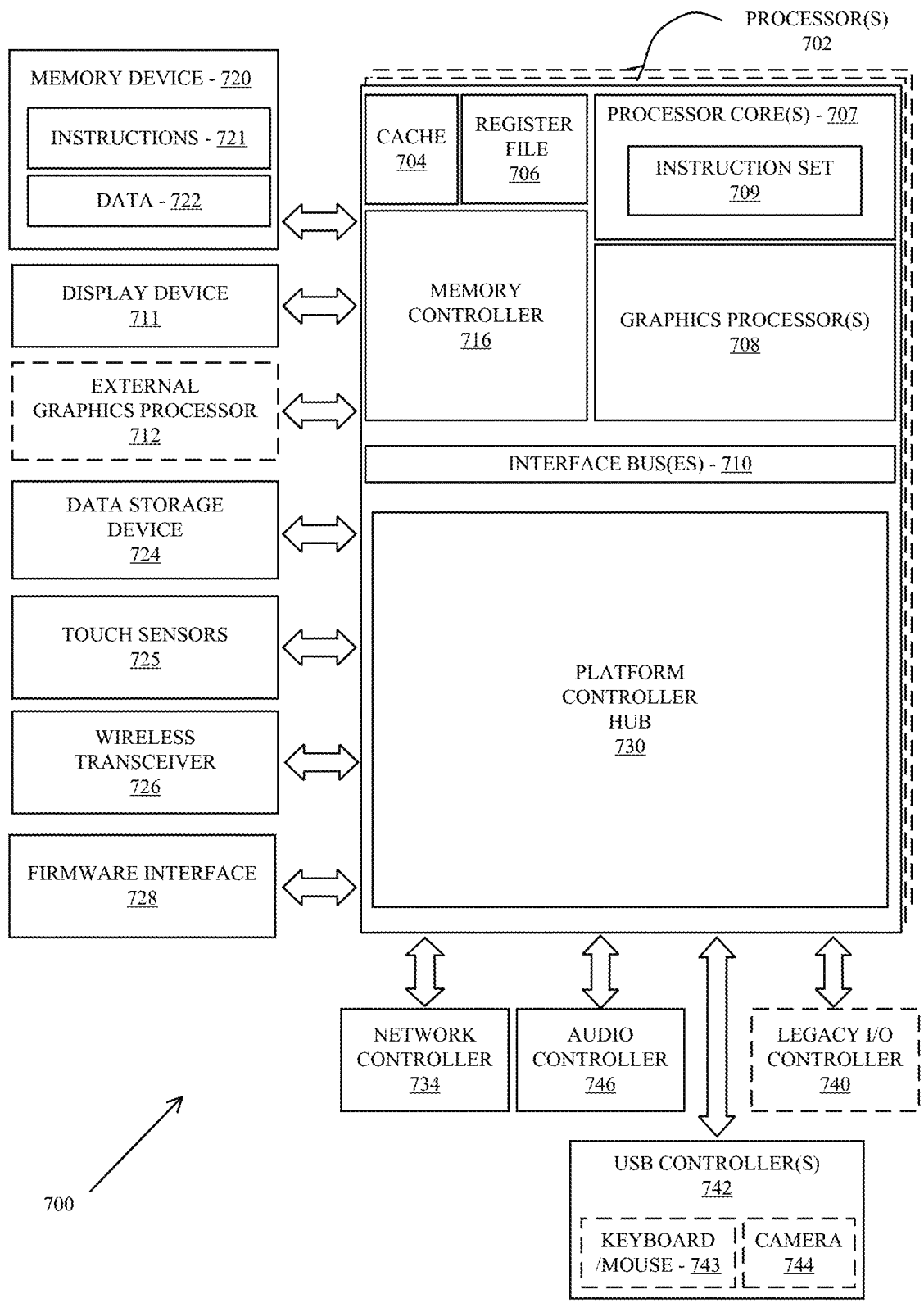
FIG. 7 is a block diagram of a processing system according to an embodiment.

FIG. 7 is a block diagram of a processing system 700, according to an embodiment. In various embodiments the system 700 includes one or more processors 702 and one or more graphics processors 708, and may be a single processor desktop system, a multiprocessor workstation system, or a server system having a large number of processors 702 or processor cores 707. In on embodiment, the system 700 is a processing platform incorporated within a system-on-a-chip (SoC or SOC) integrated circuit for use in mobile, handheld, or embedded devices.

An embodiment of system 700 can include, or be incorporated within a server-based gaming platform, a game console, including a game and media console, a mobile gaming console, a handheld game console, or an online game console. In some embodiments system 700 is a mobile phone, smart phone, tablet computing device or mobile Internet device. Data processing system 700 can also include, couple with, or be integrated within a wearable device, such as a smart watch wearable device, smart eyewear device, augmented reality device, or virtual reality device. In some embodiments, data processing system 700 is a television or set top box device having one or more processors 702 and a graphical interface generated by one or more graphics processors 708.

In some embodiments, the one or more processors 702 each include one or more processor cores 707 to process instructions which, when executed, perform operations for system and user software. In some embodiments, each of the one or more processor cores 707 is configured to process a specific instruction set 709. In some embodiments, instruction set 709 may facilitate Complex Instruction Set Computing (CISC), Reduced Instruction Set Computing (RISC), or computing via a Very Long Instruction Word (VLIW). Multiple processor cores 707 may each process a different instruction set 709, which may include instructions to facilitate the emulation of other instruction sets. Processor core 707 may also include other processing devices, such a Digital Signal Processor (DSP).

In some embodiments, the processor 702 includes cache memory 704. Depending on the architecture, the processor 702 can have a single internal cache or multiple levels of internal cache. In some embodiments, the cache memory is shared among various components of the processor 702. In some embodiments, the processor 702 also uses an external cache (e.g., a Level-3 (L3) cache or Last Level Cache (LLC)) (not shown), which may be shared among processor cores 907 using known cache coherency techniques. A register file 706 is additionally included in processor 702 which may include different types of registers for storing different types of data (e.g., integer registers, floating point registers, status registers, and an instruction pointer register). Some registers may be general-purpose registers, while other registers may be specific to the design of the processor 702.

In some embodiments, one or more processor(s) 702 are coupled with one or more interface bus(es) 710 to transmit communication signals such as address, data, or control signals between processor 702 and other components in the system. The interface bus 710, in one embodiment, can be a processor bus, such as a version of the Direct Media Interface (DMI) bus. However, processor busses are not limited to the DMI bus, and may include one or more Peripheral Component Interconnect buses (e.g., PCI, PCI Express), memory busses, or other types of interface busses. In one embodiment the processor(s) 702 include an integrated memory controller 716 and a platform controller hub 730. The memory controller 716 facilitates communication between a memory device and other components of the system 700, while the platform controller hub (PCH) 730 provides connections to I/O devices via a local I/O bus.

Memory device 720 can be a dynamic random-access memory (DRAM) device, a static random-access memory (SRAM) device, flash memory device, phase-change memory device, or some other memory device having suitable performance to serve as process memory. In one embodiment the memory device 720 can operate as system memory for the system 700, to store data 722 and instructions 721 for use when the one or more processors 702 executes an application or process. Memory controller hub 716 also couples with an optional external graphics processor 712, which may communicate with the one or more graphics processors 708 in processors 702 to perform graphics and media operations. In some embodiments a display device 711 can connect to the processor(s) 702. The display device 711 can be one or more of an internal display device, as in a mobile electronic device or a laptop device or an external display device attached via a display interface (e.g., DisplayPort, etc.). In one embodiment the display device 711 can be a head mounted display (HMD) such as a stereoscopic display device for use in virtual reality (VR) applications or augmented reality (AR) applications.

In some embodiments the platform controller hub 730 enables peripherals to connect to memory device 720 and processor 702 via a high-speed I/O bus. The I/O peripherals include, but are not limited to, an audio controller 746, a network controller 734, a firmware interface 728, a wireless transceiver 726, touch sensors 725, a data storage device 724 (e.g., hard disk drive, flash memory, etc.). The data storage device 724 can connect via a storage interface (e.g., SATA) or via a peripheral bus, such as a Peripheral Component Interconnect bus (e.g., PCI, PCI Express). The touch sensors 725 can include touch screen sensors, pressure sensors, or fingerprint sensors. The wireless transceiver 726 can be a Wi-Fi transceiver, a Bluetooth transceiver, or a mobile network transceiver such as a 3G, 4G, or Long Term Evolution (LTE) transceiver. The firmware interface 728 enables communication with system firmware, and can be, for example, a unified extensible firmware interface (UEFI). The network controller 734 can enable a network connection to a wired network. In some embodiments, a high-performance network controller (not shown) couples with the interface bus 710. The audio controller 746, in one embodiment, is a multi-channel high definition audio controller. In one embodiment the system 700 includes an optional legacy I/O controller 740 for coupling legacy (e.g., Personal System 2 (PS/2)) devices to the system. The platform controller hub 730 can also connect to one or more Universal Serial Bus (USB) controllers 742 connect input devices, such as keyboard and mouse 743 combinations, a camera 744, or other USB input devices.

Figure 8:
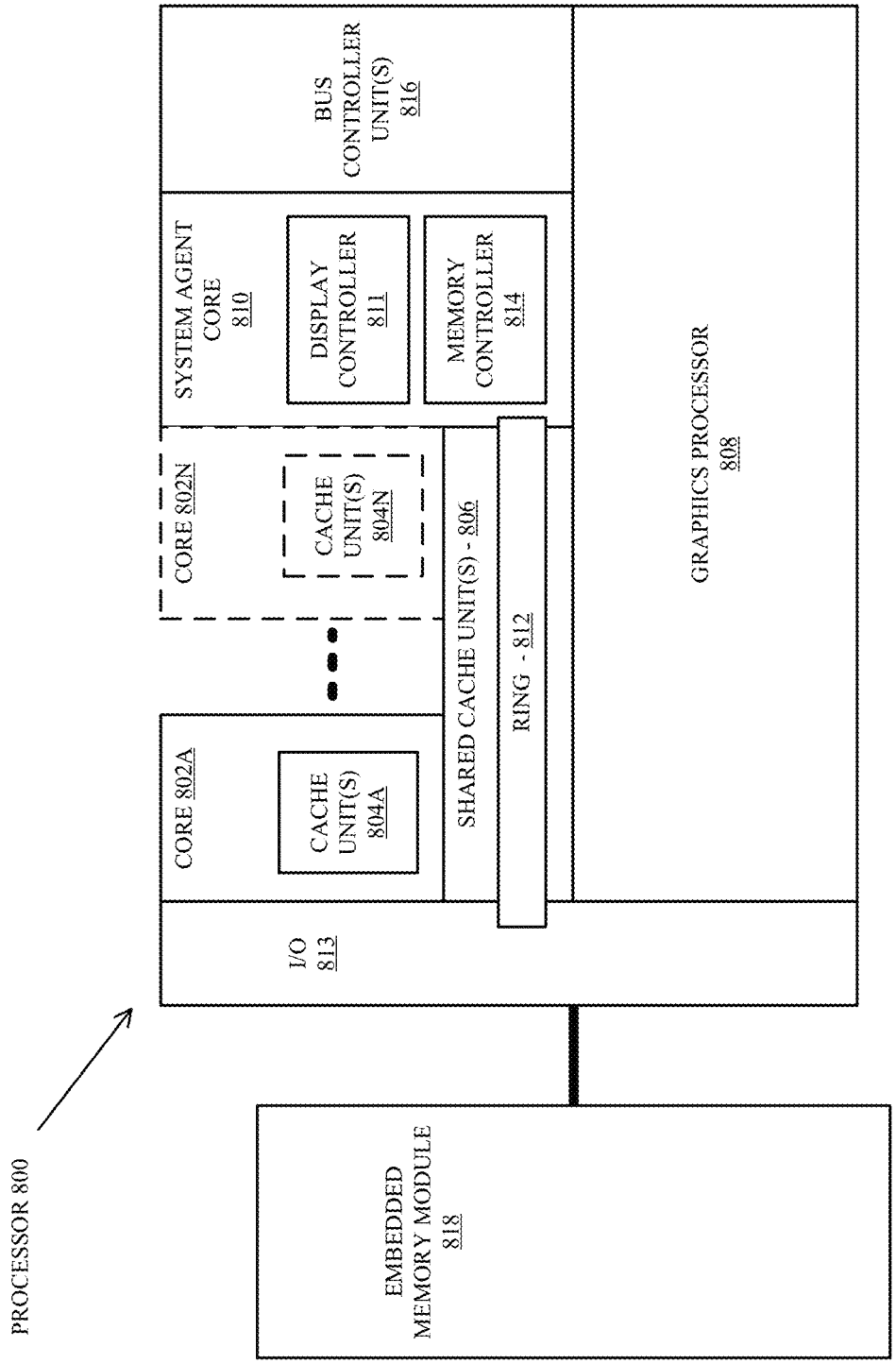
FIG. 8 is a block diagram of a processor having one or more processor cores, an integrated memory controller, and an integrated graphics processor in accordance with one or more embodiments.

FIG. 8 is a block diagram of an embodiment of a processor 800 having one or more processor cores 802A to 802N, an integrated memory controller 814, and an integrated graphics processor 808. Those elements of FIG. 8 having the same reference numbers (or names) as the elements of any other figure herein can operate or function in any manner similar to that described elsewhere herein, but are not limited to such. Processor 800 can include additional cores up to and including additional core 802N represented by the dashed lined boxes. Each of processor cores 802A to 802N includes one or more internal cache units 804A to 804N. In some embodiments each processor core also has access to one or more shared cached units 806.

The internal cache units 804A to 804N and shared cache units 806 represent a cache memory hierarchy within the processor 800. The cache memory hierarchy may include at least one level of instruction and data cache within each processor core and one or more levels of shared mid-level cache, such as a Level 2 (L2), Level 3 (L3), Level 4 (L4), or other levels of cache, where the highest level of cache before external memory is classified as the LLC. In some embodiments, cache coherency logic maintains coherency between the various cache units 806 and 804A to 804N.

In some embodiments, processor 800 may also include a set of one or more bus controller units 816 and a system agent core 810. The one or more bus controller units 816 manage a set of peripheral buses, such as one or more Peripheral Component Interconnect buses (e.g., PCI, PCI Express). System agent core 810 provides management functionality for the various processor components. In some embodiments, system agent core 810 includes one or more integrated memory controllers 814 to manage access to various external memory devices (not shown).

In some embodiments, one or more of the processor cores 802A to 802N include support for simultaneous multi-threading. In such embodiment, the system agent core 810 includes components for coordinating and operating cores 802A to 802N during multi-threaded processing. System agent core 810 may additionally include a power control unit (PCU), which includes logic and components to regulate the power state of processor cores 802A to 802N and graphics processor 808.

In some embodiments, processor 800 additionally includes graphics processor 808 to execute graphics processing operations. In some embodiments, the graphics processor 808 couples with the set of shared cache units 806, and the system agent core 810, including the one or more integrated memory controllers 814. In some embodiments, a display controller 811 is coupled with the graphics processor 808 to drive graphics processor output to one or more coupled displays. In some embodiments, display controller 811 may be a separate module coupled with the graphics processor via at least one interconnect, or may be integrated within the graphics processor 808 or system agent core 810.

In some embodiments, a ring based interconnect unit 812 is used to couple the internal components of the processor 800. However, an alternative interconnect unit may be used, such as a point-to-point interconnect, a switched interconnect, or other techniques, including techniques well known in the art. In some embodiments, graphics processor 808 couples with the ring interconnect 812 via an I/O link 813.

The exemplary I/O link 813 represents at least one of multiple varieties of I/O interconnects, including an on package I/O interconnect which facilitates communication between various processor components and a high-performance embedded memory module 818, such as an eDRAM (or embedded DRAM) module. In some embodiments, each of the processor cores 802 to 802N and graphics processor 808 use embedded memory modules 818 as a shared Last Level Cache.

In some embodiments, processor cores 802A to 802N are homogenous cores executing the same instruction set architecture. In another embodiment, processor cores 802A to 802N are heterogeneous in terms of instruction set architecture (ISA), where one or more of processor cores 802A to 802N execute a first instruction set, while at least one of the other cores executes a subset of the first instruction set or a different instruction set. In one embodiment processor cores 802A to 802N are heterogeneous in terms of microarchitecture, where one or more cores having a relatively higher power consumption couple with one or more power cores having a lower power consumption. Additionally, processor 800 can be implemented on one or more chips or as an SoC integrated circuit having the illustrated components, in addition to other components.

Figure 9:
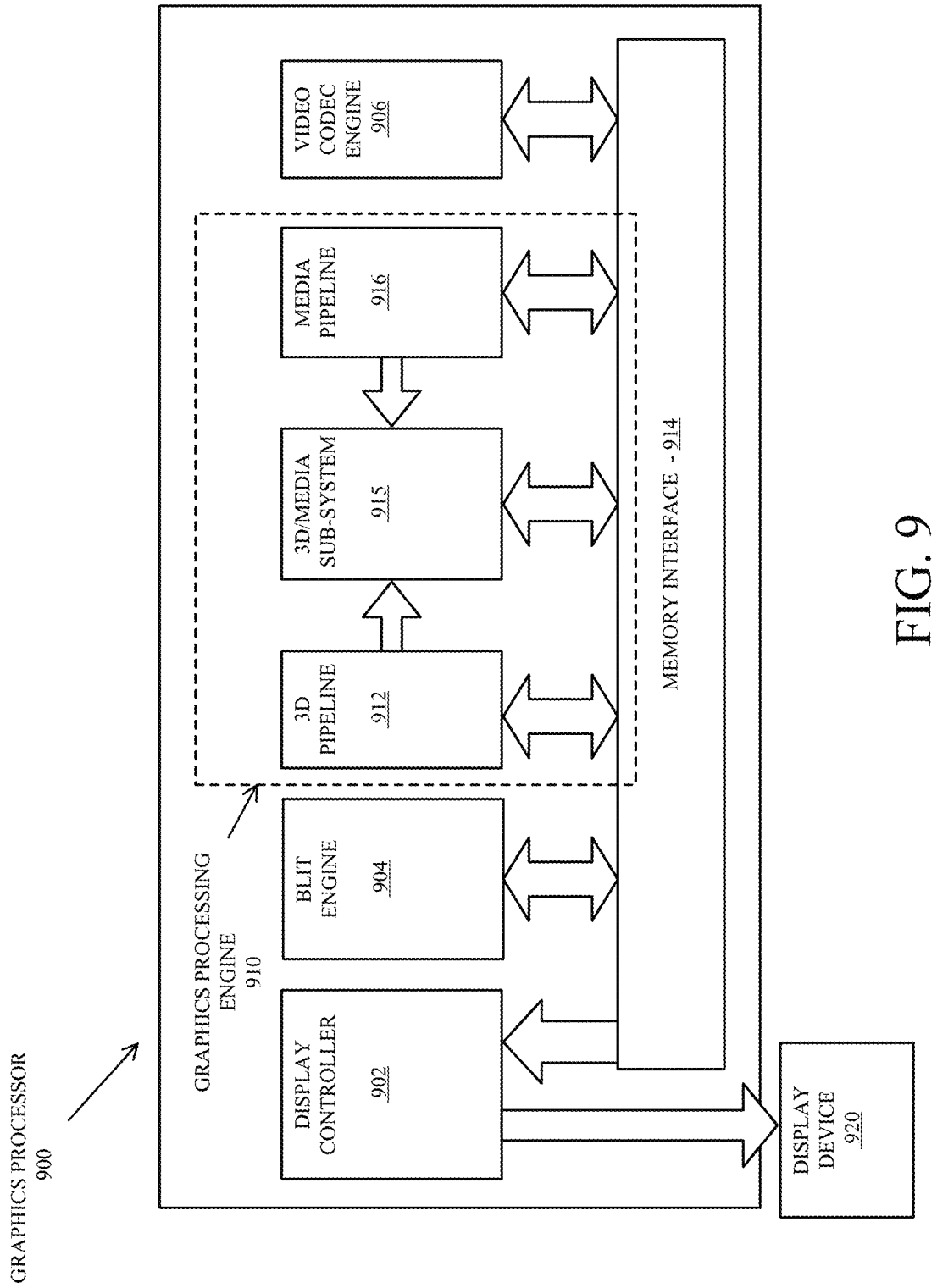
FIG. 9 is a block diagram of a graphics processor, which may be a discrete graphics processing unit, or may be a graphics processor integrated with a plurality of processing cores in accordance with one or more embodiments.

FIG. 9 is a block diagram of a graphics processor 900, which may be a discrete graphics processing unit, or may be a graphics processor integrated with a plurality of processing cores. In some embodiments, the graphics processor communicates via a memory mapped I/O interface to registers on the graphics processor and with commands placed into the processor memory. In some embodiments, graphics processor 900 includes a memory interface 914 to access memory. Memory interface 914 can be an interface to local memory, one or more internal caches, one or more shared external caches, and/or to system memory.

In some embodiments, graphics processor 900 also includes a display controller 1102 to drive display output data to a display device 920. Display controller 902 includes hardware for one or more overlay planes for the display and composition of multiple layers of video or user interface elements. In some embodiments, graphics processor 900 includes a video codec engine 906 to encode, decode, or transcode media to, from, or between one or more media encoding formats, including, but not limited to Moving Picture Experts Group (MPEG) formats such as MPEG-2, Advanced Video Coding (AVC) formats such as H.264/MPEG-4 AVC, as well as the Society of Motion Picture & Television Engineers (SMPTE) 421M/VC-1, and Joint Photographic Experts Group (JPEG) formats such as JPEG, and Motion JPEG (MJPEG) formats.

In some embodiments, graphics processor 900 includes a block image transfer (BLIT) engine 904 to perform two-dimensional (2D) rasterizer operations including, for example, bit-boundary block transfers. However, in one embodiment, 11D graphics operations are performed using one or more components of graphics processing engine (GPE) 910. In some embodiments, graphics processing engine 910 is a compute engine for performing graphics operations, including three-dimensional (3D) graphics operations and media operations.

In some embodiments, GPE 910 includes a 3D pipeline 912 for performing 3D operations, such as rendering three-dimensional images and scenes using processing functions that act upon 3D primitive shapes (e.g., rectangle, triangle, etc.). The 3D pipeline 912 includes programmable and fixed function elements that perform various tasks within the element and/or spawn execution threads to a 3D/Media sub-system 915. While 3D pipeline 912 can be used to perform media operations, an embodiment of GPE 910 also includes a media pipeline 916 that is specifically used to perform media operations, such as video post-processing and image enhancement.

In some embodiments, media pipeline 916 includes fixed function or programmable logic units to perform one or more specialized media operations, such as video decode acceleration, video de-interlacing, and video encode acceleration in place of, or on behalf of video codec engine 906. In some embodiments, media pipeline 916 additionally includes a thread spawning unit to spawn threads for execution on 3D/Media sub-system 915. The spawned threads perform computations for the media operations on one or more graphics execution units included in 3D/Media subsystem 915.

In some embodiments, 3D/Media subsystem 915 includes logic for executing threads spawned by 3D pipeline 912 and media pipeline 916. In one embodiment, the pipelines send thread execution requests to 3D/Media subsystem 915, which includes thread dispatch logic for arbitrating and dispatching the various requests to available thread execution resources. The execution resources include an array of graphics execution units to process the 3D and media threads. In some embodiments, 3D/Media subsystem 915 includes one or more internal caches for thread instructions and data. In some embodiments, the subsystem also includes shared memory, including registers and addressable memory, to share data between threads and to store output data.

Figure 10:
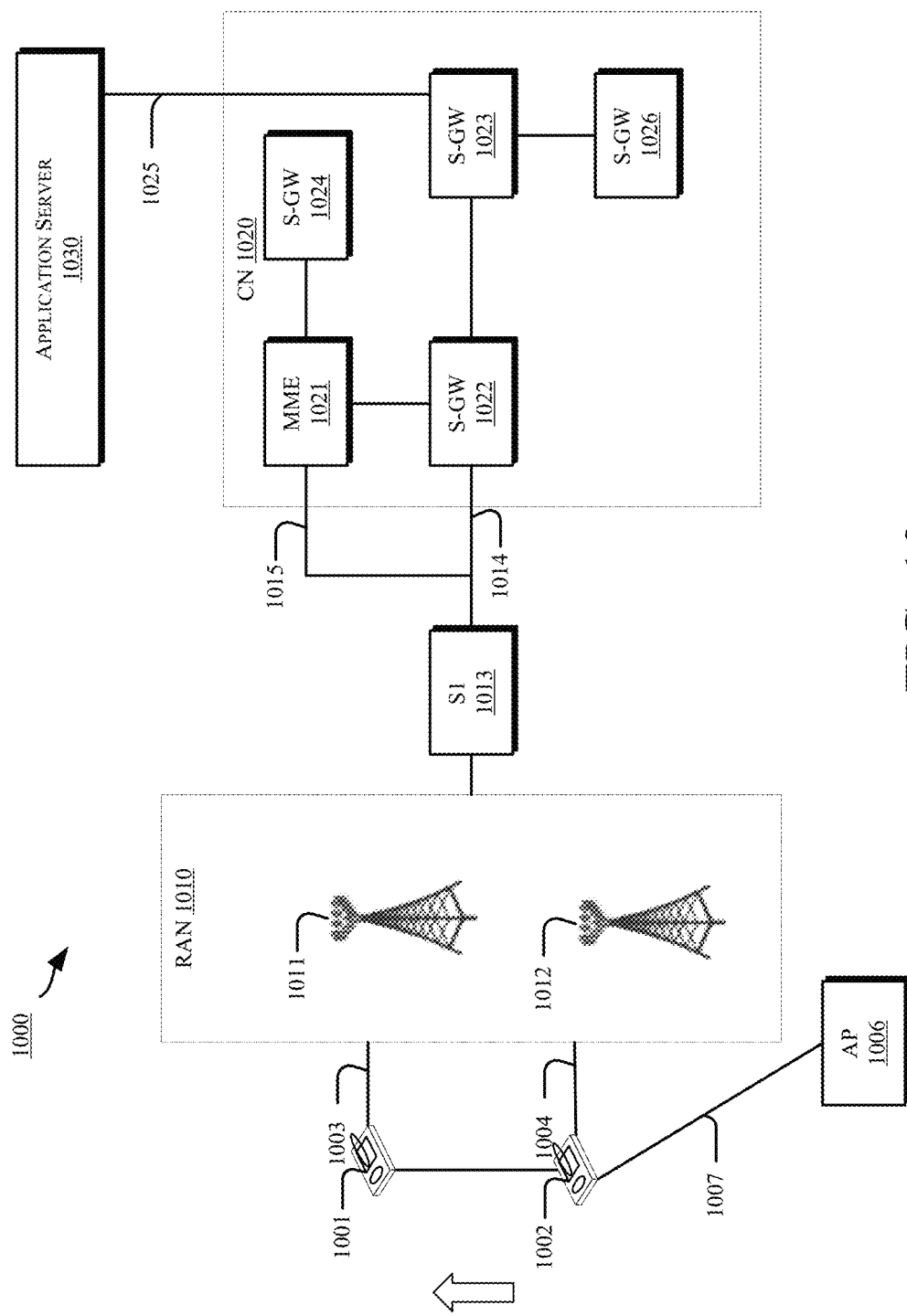
FIG. 10 illustrates an architecture of a system of a network in accordance with one or more embodiments.

FIG. 10 illustrates an architecture of a system 1000 of a network in accordance with some embodiments. The system 1000 is shown to include a user equipment (UE) 1001 and a UE 1002. The UEs 1001 and 1002 are illustrated as smartphones (e.g., handheld touchscreen mobile computing devices connectable to one or more cellular networks), but may also comprise any mobile or non-mobile computing device, such as Personal Data Assistants (PDAs), pagers, laptop computers, desktop computers, wireless handsets, automobile or automobile system, or any computing device including a wireless communications interface.

In some embodiments, any of the UEs 1001 and 1002 can comprise an Internet of Things (IoT) UE, which can comprise a network access layer designed for low-power IoT applications utilizing short-lived UE connections. An IoT UE can utilize technologies such as machine-to-machine (M2M) or machine-type communications (MTC) for exchanging data with an MTC server or device via a public land mobile network (PLMN), Proximity-Based Service (ProSe) or device-to-device (D2D) communication, sensor networks, or IoT networks. The M2M or MTC exchange of data may be a machine-initiated exchange of data. An IoT network describes interconnecting IoT UEs, which may include uniquely identifiable embedded computing devices (within the Internet infrastructure), with short-lived connections. The IoT UEs may execute background applications (e.g., keep-alive messages, status updates, etc.) to facilitate the connections of the IoT network.

The UEs 1001 and 1002 may be configured to connect, e.g., communicatively couple, with a radio access network (RAN) 1010—the RAN 1010 may be, for example, an Evolved Universal Mobile Telecommunications System (UMTS) Terrestrial Radio Access Network (E-UTRAN), a NextGen RAN (NG RAN), or some other type of RAN. The UEs 1001 and 1002 utilize connections 1003 and 1004, respectively, each of which comprises a physical communications interface or layer (discussed in further detail below); in this example, the connections 1003 and 1004 are illustrated as an air interface to enable communicative coupling, and can be consistent with cellular communications protocols, such as a Global System for Mobile Communications (GSM) protocol, a code-division multiple access (CDMA) network protocol, a Push-to-Talk (PTT) protocol, a PTT over Cellular (POC) protocol, a Universal Mobile Telecommunications System (UMTS) protocol, a 3GPP Long Term Evolution (LTE) protocol, a fifth generation (5G) protocol, a New Radio (NR) protocol, and the like.

In this embodiment, the UEs 1001 and 1002 may further directly exchange communication data via a ProSe interface 1005. The ProSe interface 1005 may alternatively be referred to as a sidelink interface comprising one or more logical channels, including but not limited to a Physical Sidelink Control Channel (PSCCH), a Physical Sidelink Shared Channel (PSSCH), a Physical Sidelink Discovery Channel (PSDCH), and a Physical Sidelink Broadcast Channel (PSBCH).

The UE 1002 is shown to be configured to access an access point (AP) 1006 via connection 1007. The connection 1007 can comprise a local wireless connection, such as a connection consistent with any IEEE 802.11 protocol, wherein the AP 1006 would comprise a wireless fidelity (WiFi®) router. In this example, the AP 1006 is shown to be connected to the Internet without connecting to the core network of the wireless system (described in further detail below).

The RAN 1010 can include one or more access nodes that enable the connections 1003 and 1004. These access nodes (ANs) can be referred to as base stations (BSs), NodeBs, evolved NodeBs (eNBs), next Generation NodeBs (gNB), RAN nodes, and so forth, and can comprise ground stations (e.g., terrestrial access points) or satellite stations providing coverage within a geographic area (e.g., a cell). The RAN 1010 may include one or more RAN nodes for providing macrocells, e.g., macro RAN node 1011, and one or more RAN nodes for providing femtocells or picocells (e.g., cells having smaller coverage areas, smaller user capacity, or higher bandwidth compared to macrocells), e.g., low power (LP) RAN node 1012.

Any of the RAN nodes 1011 and 1012 can terminate the air interface protocol and can be the first point of contact for the UEs 1001 and 1002. In some embodiments, any of the RAN nodes 1011 and 1012 can fulfill various logical functions for the RAN 1010 including, but not limited to, radio network controller (RNC) functions such as radio bearer management, uplink and downlink dynamic radio resource management and data packet scheduling, and mobility management.

In accordance with some embodiments, the UEs 1001 and 1002 can be configured to communicate using Orthogonal Frequency-Division Multiplexing (OFDM) communication signals with each other or with any of the RAN nodes 1011 and 1012 over a multicarrier communication channel in accordance various communication techniques, such as, but not limited to, an Orthogonal Frequency-Division Multiple Access (OFDMA) communication technique (e.g., for downlink communications) or a Single Carrier Frequency Division Multiple Access (SC-FDMA) communication technique (e.g., for uplink and ProSe or sidelink communications), although the scope of the embodiments is not limited in this respect. The OFDM signals can comprise a plurality of orthogonal subcarriers.

In some embodiments, a downlink resource grid can be used for downlink transmissions from any of the RAN nodes 1011 and 1012 to the UEs 1001 and 1002, while uplink transmissions can utilize similar techniques. The grid can be a time-frequency grid, called a resource grid or time-frequency resource grid, which is the physical resource in the downlink in each slot. Such a time-frequency plane representation is a common practice for OFDM systems, which makes it intuitive for radio resource allocation. Each column and each row of the resource grid corresponds to one OFDM symbol and one OFDM subcarrier, respectively. The duration of the resource grid in the time domain corresponds to one slot in a radio frame. The smallest time-frequency unit in a resource grid is denoted as a resource element. Each resource grid comprises a number of resource blocks, which describe the mapping of certain physical channels to resource elements. Each resource block comprises a collection of resource elements; in the frequency domain, this may represent the smallest quantity of resources that currently can be allocated. There are several different physical downlink channels that are conveyed using such resource blocks.

The physical downlink shared channel (PDSCH) may carry user data and higher-layer signaling to the UEs 1001 and 1002. The physical downlink control channel (PDCCH) may carry information about the transport format and resource allocations related to the PDSCH channel, among other things. It may also inform the UEs 1001 and 1002 about the transport format, resource allocation, and H-ARQ (Hybrid Automatic Repeat Request) information related to the uplink shared channel. Typically, downlink scheduling (assigning control and shared channel resource blocks to the UE 102 within a cell) may be performed at any of the RAN nodes 1011 and 1012 based on channel quality information fed back from any of the UEs 1001 and 1002. The downlink resource assignment information may be sent on the PDCCH used for (e.g., assigned to) each of the UEs 1001 and 1002.

The PDCCH may use control channel elements (CCEs) to convey the control information. Before being mapped to resource elements, the PDCCH complex-valued symbols may first be organized into quadruplets, which may then be permuted using a sub-block interleaver for rate matching. Each PDCCH may be transmitted using one or more of these CCEs, where each CCE may correspond to nine sets of four physical resource elements known as resource element groups (REGs). Four Quadrature Phase Shift Keying (QPSK) symbols may be mapped to each REG. The PDCCH can be transmitted using one or more CCEs, depending on the size of the downlink control information (DCI) and the channel condition. There can be four or more different PDCCH formats defined in LTE with different numbers of CCEs (e.g., aggregation level, L=1, 2, 4, or 8).

Some embodiments may use concepts for resource allocation for control channel information that are an extension of the above-described concepts. For example, some embodiments may utilize an enhanced physical downlink control channel (EPDCCH) that uses PDSCH resources for control information transmission. The EPDCCH may be transmitted using one or more enhanced the control channel elements (ECCEs). Similar to above, each ECCE may correspond to nine sets of four physical resource elements known as an enhanced resource element groups (EREGs). An ECCE may have other numbers of EREGs in some situations.

The RAN 1010 is shown to be communicatively coupled to a core network (CN) 1020—via an S1 interface 1013. In embodiments, the CN 1020 may be an evolved packet core (EPC) network, a NextGen Packet Core (NPC) network, or some other type of CN. In this embodiment the S1 interface 1013 is split into two parts: the S1-U interface 1014, which carries traffic data between the RAN nodes 1011 and 1012 and the serving gateway (S-GW) 1022, and the S1-mobility management entity (MME) interface 1015, which is a signaling interface between the RAN nodes 1011 and 1012 and MMEs 1021.

In this embodiment, the CN 1020 comprises the MMEs 1021, the S-GW 1022, the Packet Data Network (PDN) Gateway (P-GW) 1023, and a home subscriber server (HSS)

1024. The MMEs 1021 may be similar in function to the control plane of legacy Serving General Packet Radio Service (GPRS) Support Nodes (SGSN). The MMEs 1021 may manage mobility aspects in access such as gateway selection and tracking area list management. The HSS 1024 may comprise a database for network users, including subscription-related information to support the network entities' handling of communication sessions. The CN 1020 may comprise one or several HSSs 1024, depending on the number of mobile subscribers, on the capacity of the equipment, on the organization of the network, etc. For example, the HSS 1024 can provide support for routing/roaming, authentication, authorization, naming/addressing resolution, location dependencies, etc.

The S-GW 1022 may terminate the S1 interface 1013 towards the RAN 1010, and routes data packets between the RAN 1010 and the CN 1020. In addition, the S-GW 1022 may be a local mobility anchor point for inter-RAN node handovers and also may provide an anchor for inter-3GPP mobility. Other responsibilities may include lawful intercept, charging, and some policy enforcement.

The P-GW 1023 may terminate an SGi interface toward a PDN. The P-GW 1023 may route data packets between the EPC network 1023 and external networks such as a network including the application server 1030 (alternatively referred to as application function (AF)) via an Internet Protocol (IP) interface 1025. Generally, the application server 1030 may be an element offering applications that use IP bearer resources with the core network (e.g., UMTS Packet Services (PS) domain, LTE PS data services, etc.). In this embodiment, the P-GW 1023 is shown to be communicatively coupled to an application server 1030 via an IP communications interface 1025. The application server 1030 can also be configured to support one or more communication services (e.g., Voice-over-Internet Protocol (VoIP) sessions, PTT sessions, group communication sessions, social networking services, etc.) for the UEs 1001 and 1002 via the CN 1020.

The P-GW 1023 may further be a node for policy enforcement and charging data collection. Policy and Charging Enforcement Function (PCRF) 1026 is the policy and charging control element of the CN 1020. In a non-roaming scenario, there may be a single PCRF in the Home Public Land Mobile Network (HPLMN) associated with a UE's Internet Protocol Connectivity Access Network (IP-CAN) session. In a roaming scenario with local breakout of traffic, there may be two PCRFs associated with a UE's IP-CAN session: a Home PCRF (H-PCRF) within a HPLMN and a Visited PCRF (V-PCRF) within a Visited Public Land Mobile Network (VPLMN). The PCRF 1026 may be communicatively coupled to the application server 1030 via the P-GW 1023. The application server 1030 may signal the PCRF 1026 to indicate a new service flow and select the appropriate Quality of Service (QoS) and charging parameters. The PCRF 1026 may provision this rule into a Policy and Charging Enforcement Function (PCEF) (not shown) with the appropriate traffic flow template (TFT) and QoS class of identifier (QCI), which commences the QoS and charging as specified by the application server 1030.

Figure 11:
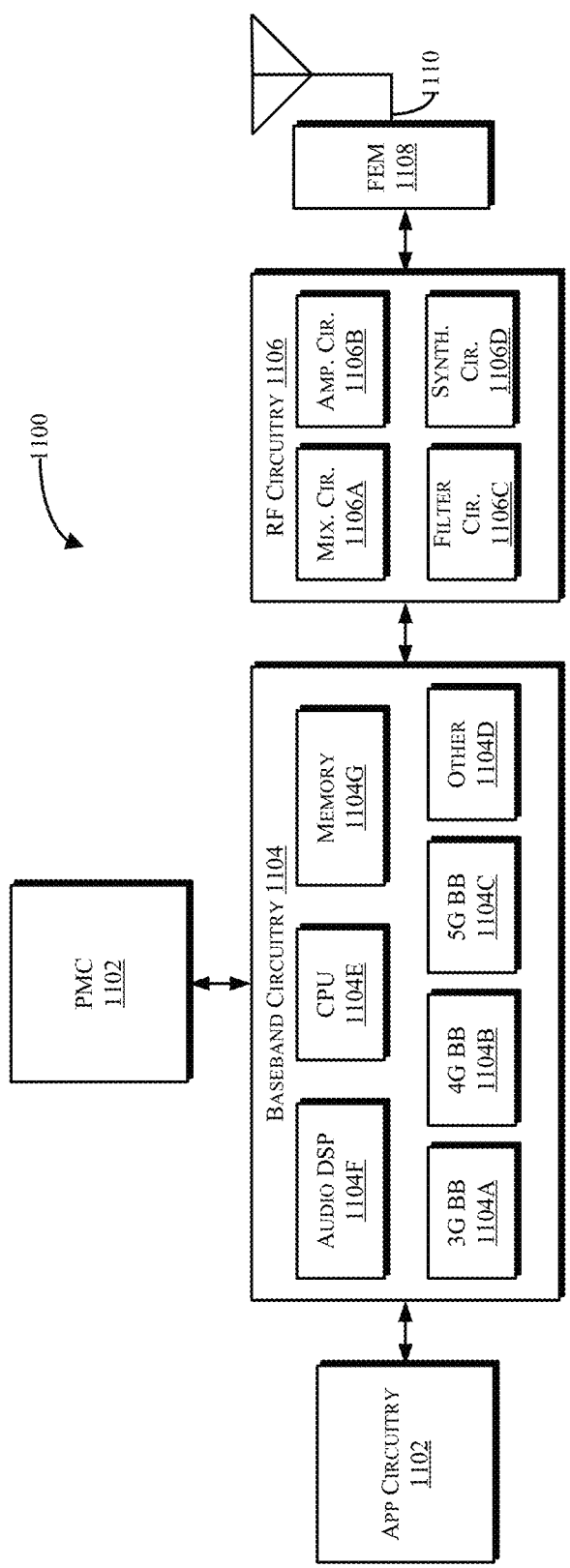
FIG. 11 illustrates example components of a wireless communication device in accordance with one or more embodiments.

FIG. 11 illustrates example components of a device in accordance with some embodiments. In some embodiments, the device 1100 may include application circuitry 1102, baseband circuitry 1104, Radio Frequency (RF) circuitry 1106, front-end module (FEM) circuitry 1108, one or more antennas 1110, and power management circuitry (PMC) 1112 coupled together at least as shown. The components of the illustrated device 1100 may be included in a UE or a RAN node. In some embodiments, the device 1100 may include less elements (e.g., a RAN node may not utilize application circuitry 1102, and instead include a processor/controller to process IP data received from an EPC). In some embodiments, the device 1100 may include additional elements such as, for example, memory/storage, display, camera, sensor, or input/output (I/O) interface. In other embodiments, the components described below may be included in more than one device (e.g., said circuitries may be separately included in more than one device for Cloud-RAN (C-RAN) implementations).

The application circuitry 1102 may include one or more application processors. For example, the application circuitry 1102 may include circuitry such as, but not limited to, one or more single-core or multi-core processors. The processor(s) may include any combination of general-purpose processors and dedicated processors (e.g., graphics processors, application processors, etc.). The processors may be coupled with or may include memory/storage and may be configured to execute instructions stored in the memory/storage to enable various applications or operating systems to run on the device 1100. In some embodiments, processors of application circuitry 1102 may process IP data packets received from an EPC.

The baseband circuitry 1104 may include circuitry such as, but not limited to, one or more single-core or multi-core processors. The baseband circuitry 1104 may include one or more baseband processors or control logic to process baseband signals received from a receive signal path of the RF circuitry 1106 and to generate baseband signals for a transmit signal path of the RF circuitry 1106. Baseband processing circuitry 1104 may interface with the application circuitry 1102 for generation and processing of the baseband signals and for controlling operations of the RF circuitry 1106. For example, in some embodiments, the baseband circuitry 1104 may include a third generation (3G) baseband processor 1104A, a fourth generation (4G) baseband processor 1104B, a fifth generation (5G) baseband processor 1104C, or other baseband processor(s) 1104D for other existing generations, generations in development or to be developed in the future (e.g., second generation (2G), sixth generation (6G), etc.). The baseband circuitry 1104 (e.g., one or more of baseband processors 1104A-D) may handle various radio control functions that enable communication with one or more radio networks via the RF circuitry 1106. In other embodiments, some or all of the functionality of baseband processors 1104A-D may be included in modules stored in the memory 1104G and executed via a Central Processing Unit (CPU) 1104E. The radio control functions may include, but are not limited to, signal modulation/demodulation, encoding/decoding, radio frequency shifting, etc. In some embodiments, modulation/demodulation circuitry of the baseband circuitry 1104 may include Fast-Fourier Transform (FFT), precoding, or constellation mapping/demapping functionality. In some embodiments, encoding/decoding circuitry of the baseband circuitry 1104 may include convolution, tail-biting convolution, turbo, Viterbi, or Low Density Parity Check (LDPC) encoder/decoder functionality. Embodiments of modulation/demodulation and encoder/decoder functionality are not limited to these examples and may include other suitable functionality in other embodiments.

In some embodiments, the baseband circuitry 1104 may include one or more audio digital signal processor(s) (DSP) 1104F. The audio DSP(s) 1104F may be include elements for compression/decompression and echo cancellation and may include other suitable processing elements in other embodiments. Components of the baseband circuitry may be suitably combined in a single chip, a single chipset, or disposed on a same circuit board in some embodiments. In some embodiments, some or all of the constituent components of the baseband circuitry 1104 and the application circuitry 1102 may be implemented together such as, for example, on a system on a chip (SOC).

In some embodiments, the baseband circuitry 1104 may provide for communication compatible with one or more radio technologies. For example, in some embodiments, the baseband circuitry 1104 may support communication with an evolved universal terrestrial radio access network (EUTRAN) or other wireless metropolitan area networks (WMAN), a wireless local area network (WLAN), a wireless personal area network (WPAN). Embodiments in which the baseband circuitry 1104 is configured to support radio communications of more than one wireless protocol may be referred to as multi-mode baseband circuitry.

RF circuitry 1106 may enable communication with wireless networks using modulated electromagnetic radiation through a non-solid medium. In various embodiments, the RF circuitry 1106 may include switches, filters, amplifiers, etc. to facilitate the communication with the wireless network. RF circuitry 1106 may include a receive signal path which may include circuitry to down-convert RF signals received from the FEM circuitry 1108 and provide baseband signals to the baseband circuitry 1104. RF circuitry 1106 may also include a transmit signal path which may include circuitry to up-convert baseband signals provided by the baseband circuitry 1104 and provide RF output signals to the FEM circuitry 1108 for transmission.

In some embodiments, the receive signal path of the RF circuitry 1106 may include mixer circuitry 1106a, amplifier circuitry 1106b and filter circuitry 1106c. In some embodiments, the transmit signal path of the RF circuitry 1106 may include filter circuitry 1106c and mixer circuitry 1106a. RF circuitry 1106 may also include synthesizer circuitry 1106d for synthesizing a frequency for use by the mixer circuitry 1106a of the receive signal path and the transmit signal path. In some embodiments, the mixer circuitry 1106a of the receive signal path may be configured to down-convert RF signals received from the FEM circuitry 1108 based on the synthesized frequency provided by synthesizer circuitry 1106d. The amplifier circuitry 1106b may be configured to amplify the down-converted signals and the filter circuitry 1106c may be a low-pass filter (LPF) or band-pass filter (BPF) configured to remove unwanted signals from the down-converted signals to generate output baseband signals. Output baseband signals may be provided to the baseband circuitry 1104 for further processing. In some embodiments, the output baseband signals may be zero-frequency baseband signals, although this is not a requirement. In some embodiments, mixer circuitry 1106a of the receive signal path may comprise passive mixers, although the scope of the embodiments is not limited in this respect.

In some embodiments, the mixer circuitry 1106a of the transmit signal path may be configured to up-convert input baseband signals based on the synthesized frequency provided by the synthesizer circuitry 1106d to generate RF output signals for the FEM circuitry 1108. The baseband signals may be provided by the baseband circuitry 1104 and may be filtered by filter circuitry 1106c.

In some embodiments, the mixer circuitry 1106a of the receive signal path and the mixer circuitry 1106a of the transmit signal path may include two or more mixers and may be arranged for quadrature downconversion and upconversion, respectively. In some embodiments, the mixer circuitry 1106a of the receive signal path and the mixer circuitry 1106a of the transmit signal path may include two or more mixers and may be arranged for image rejection (e.g., Hartley image rejection). In some embodiments, the mixer circuitry 1106a of the receive signal path and the mixer circuitry 1106a may be arranged for direct downconversion and direct upconversion, respectively. In some embodiments, the mixer circuitry 1106a of the receive signal path and the mixer circuitry 1106a of the transmit signal path may be configured for super-heterodyne operation.

In some embodiments, the output baseband signals and the input baseband signals may be analog baseband signals, although the scope of the embodiments is not limited in this respect. In some alternate embodiments, the output baseband signals and the input baseband signals may be digital baseband signals. In these alternate embodiments, the RF circuitry 1106 may include analog-to-digital converter (ADC) and digital-to-analog converter (DAC) circuitry and the baseband circuitry 1104 may include a digital baseband interface to communicate with the RF circuitry 1106.

In some dual-mode embodiments, a separate radio IC circuitry may be provided for processing signals for each spectrum, although the scope of the embodiments is not limited in this respect.

In some embodiments, the synthesizer circuitry 1106d may be a fractional-N synthesizer or a fractional N/N+1 synthesizer, although the scope of the embodiments is not limited in this respect as other types of frequency synthesizers may be suitable. For example, synthesizer circuitry 1106d may be a delta-sigma synthesizer, a frequency multiplier, or a synthesizer comprising a phase-locked loop with a frequency divider.

The synthesizer circuitry 1106d may be configured to synthesize an output frequency for use by the mixer circuitry 1106a of the RF circuitry 1106 based on a frequency input and a divider control input. In some embodiments, the synthesizer circuitry 1106d may be a fractional N/N+1 synthesizer.

In some embodiments, frequency input may be provided by a voltage controlled oscillator (VCO), although that is not a requirement. Divider control input may be provided by either the baseband circuitry 1104 or the applications processor 1102 depending on the desired output frequency. In some embodiments, a divider control input (e.g., N) may be determined from a look-up table based on a channel indicated by the applications processor 1102.

Synthesizer circuitry 1106d of the RF circuitry 1106 may include a divider, a delay-locked loop (DLL), a multiplexer and a phase accumulator. In some embodiments, the divider may be a dual modulus divider (DMD) and the phase accumulator may be a digital phase accumulator (DPA). In some embodiments, the DMD may be configured to divide the input signal by either N or N+1 (e.g., based on a carry out) to provide a fractional division ratio. In some example embodiments, the DLL may include a set of cascaded, tunable, delay elements, a phase detector, a charge pump and a D-type flip-flop. In these embodiments, the delay elements may be configured to break a VCO period up into Nd equal packets of phase, where Nd is the number of delay elements in the delay line. In this way, the DLL provides negative feedback to help ensure that the total delay through the delay line is one VCO cycle.

In some embodiments, synthesizer circuitry 1106d may be configured to generate a carrier frequency as the output frequency, while in other embodiments, the output frequency may be a multiple of the carrier frequency (e.g., twice the carrier frequency, four times the carrier frequency)

and used in conjunction with quadrature generator and divider circuitry to generate multiple signals at the carrier frequency with multiple different phases with respect to each other. In some embodiments, the output frequency may be a LO frequency (fLO). In some embodiments, the RF circuitry 1106 may include an IQ/polar converter.

FEM circuitry 1108 may include a receive signal path which may include circuitry configured to operate on RF signals received from one or more antennas 1110, amplify the received signals and provide the amplified versions of the received signals to the RF circuitry 1106 for further processing. FEM circuitry 1108 may also include a transmit signal path which may include circuitry configured to amplify signals for transmission provided by the RF circuitry 1106 for transmission by one or more of the one or more antennas 1110. In various embodiments, the amplification through the transmit or receive signal paths may be done solely in the RF circuitry 1106, solely in the FEM 1108, or in both the RF circuitry 1106 and the FEM 1108.

In some embodiments, the FEM circuitry 1108 may include a TX/RX switch to switch between transmit mode and receive mode operation. The FEM circuitry may include a receive signal path and a transmit signal path. The receive signal path of the FEM circuitry may include an LNA to amplify received RF signals and provide the amplified received RF signals as an output (e.g., to the RF circuitry 1106). The transmit signal path of the FEM circuitry 1108 may include a power amplifier (PA) to amplify input RF signals (e.g., provided by RF circuitry 1106), and one or more filters to generate RF signals for subsequent transmission (e.g., by one or more of the one or more antennas 1110).

In some embodiments, the PMC 1112 may manage power provided to the baseband circuitry 1104. In particular, the PMC 1112 may control power-source selection, voltage scaling, battery charging, or DC-to-DC conversion. The PMC 1112 may often be included when the device 1100 is capable of being powered by a battery, for example, when the device is included in a UE. The PMC 1112 may increase the power conversion efficiency while providing desirable implementation size and heat dissipation characteristics.

While FIG. 11 shows the PMC 1112 coupled only with the baseband circuitry 1104. However, in other embodiments, the PMC 11 12 may be additionally or alternatively coupled with, and perform similar power management operations for, other components such as, but not limited to, application circuitry 1102, RF circuitry 1106, or FEM 1108.

In some embodiments, the PMC 1112 may control, or otherwise be part of, various power saving mechanisms of the device 1100. For example, if the device 1100 is in an RRC_Connected state, where it is still connected to the RAN node as it expects to receive traffic shortly, then it may enter a state known as Discontinuous Reception Mode (DRX) after a period of inactivity. During this state, the device 1100 may power down for brief intervals of time and thus save power.

If there is no data traffic activity for an extended period of time, then the device 1100 may transition off to an RRC_Idle state, where it disconnects from the network and does not perform operations such as channel quality feedback, handover, etc. The device 1100 goes into a very low power state and it performs paging where again it periodically wakes up to listen to the network and then powers down again. The device 1100 may not receive data in this state, in order to receive data, it must transition back to RRC_Connected state.

An additional power saving mode may allow a device to be unavailable to the network for periods longer than a paging interval (ranging from seconds to a few hours). During this time, the device is totally unreachable to the network and may power down completely. Any data sent during this time incurs a large delay and it is assumed the delay is acceptable.

Processors of the application circuitry 1102 and processors of the baseband circuitry 1104 may be used to execute elements of one or more instances of a protocol stack. For example, processors of the baseband circuitry 1104, alone or in combination, may be used execute Layer 3, Layer 2, or Layer 1 functionality, while processors of the application circuitry 1104 may utilize data (e.g., packet data) received from these layers and further execute Layer 4 functionality (e.g., transmission communication protocol (TCP) and user datagram protocol (UDP) layers). As referred to herein, Layer 3 may comprise a radio resource control (RRC) layer, described in further detail below. As referred to herein, Layer 2 may comprise a medium access control (MAC) layer, a radio link control (RLC) layer, and a packet data convergence protocol (PDCP) layer, described in further detail below. As referred to herein, Layer 1 may comprise a physical (PHY) layer of a UE/RAN node, described in further detail below.

Figure 12:
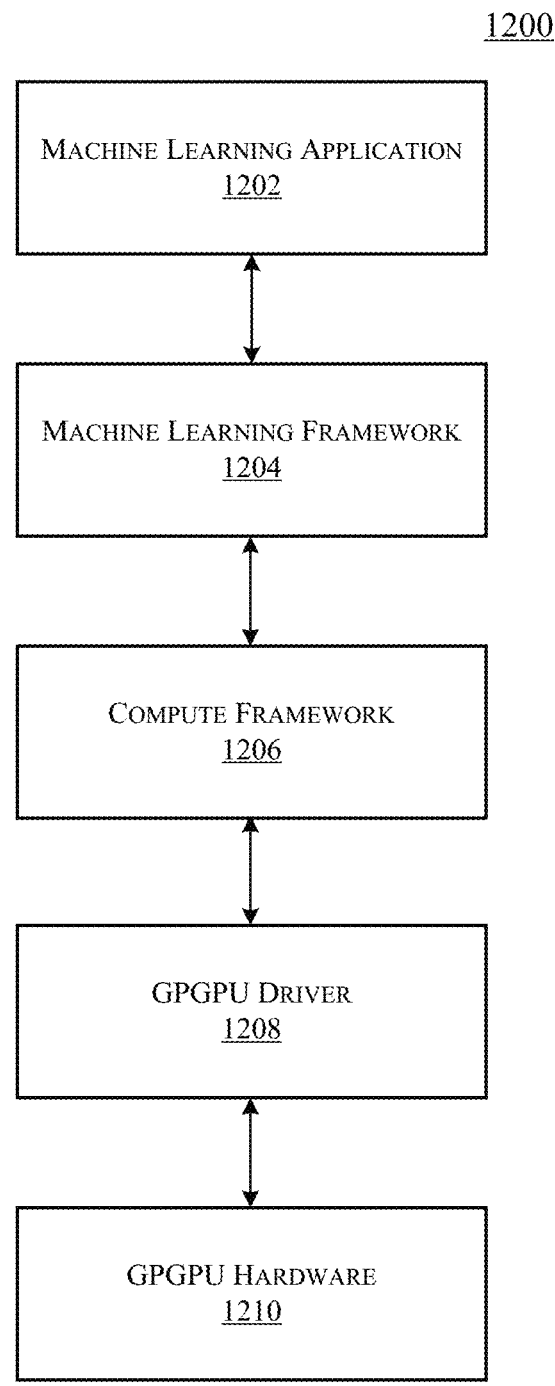
FIG. 12 is a generalized diagram of a machine learning software stack in accordance with one or more embodiments.

FIG. 12 is a generalized diagram of a machine learning software stack 1200. A machine learning application 1202 can be configured to train a neural network using a training dataset or to use a trained deep neural network to implement machine intelligence. The machine learning application 1202 can include training and inference functionality for a neural network and/or specialized software that can be used to train a neural network before deployment. The machine learning application 1202 can implement any type of machine intelligence including but not limited to image recognition, mapping and localization, autonomous navigation, speech synthesis, medical imaging, or language translation.

Hardware acceleration for the machine learning application 1202 can be enabled via a machine learning framework 1204. The machine learning framework 1204 can provide a library of machine learning primitives. Machine learning primitives are basic operations that are commonly performed by machine learning algorithms. Without the machine learning framework 1204, developers of machine learning algorithms would be required to create and optimize the main computational logic associated with the machine learning algorithm, then re-optimize the computational logic as new parallel processors are developed. Instead, the machine learning application can be configured to perform the necessary computations using the primitives provided by the machine learning framework 1204. Exemplary primitives include tensor convolutions, activation functions, and pooling, which are computational operations that are performed while training a convolutional neural network (CNN). The machine learning framework 1204 can also provide primitives to implement basic linear algebra subprograms performed by many machine-learning algorithms, such as matrix and vector operations.

The machine learning framework 1204 can process input data received from the machine learning application 1202 and generate the appropriate input to a compute framework 1206. The compute framework 1206 can abstract the underlying instructions provided to the GPGPU driver 1208 to enable the machine learning framework 1204 to take advantage of hardware acceleration via the GPGPU hardware 1210 without requiring the machine learning framework 1204 to have intimate knowledge of the architecture of the GPGPU hardware 1210. Additionally, the compute framework 1206 can enable hardware acceleration for the machine learning framework 1204 across a variety of types and generations of the GPGPU hardware 1210.

The computing architecture provided by embodiments described herein can be configured to perform the types of parallel processing that is particularly suited for training and deploying neural networks for machine learning. A neural network can be generalized as a network of functions having a graph relationship. As is known in the art, there are a variety of types of neural network implementations used in machine learning. One exemplary type of neural network is the feedforward network, as previously described.

A second exemplary type of neural network is the Convolutional Neural Network (CNN). A CNN is a specialized feedforward neural network for processing data having a known, grid-like topology, such as image data. Accordingly, CNNs are commonly used for compute vision and image recognition applications, but they also may be used for other types of pattern recognition such as speech and language processing. The nodes in the CNN input layer are organized into a set of "filters" (feature detectors inspired by the receptive fields found in the retina), and the output of each set of filters is propagated to nodes in successive layers of the network. The computations for a CNN include applying the convolution mathematical operation to each filter to produce the output of that filter. Convolution is a specialized kind of mathematical operation performed by two functions to produce a third function that is a modified version of one of the two original functions. In convolutional network terminology, the first function to the convolution can be referred to as the input, while the second function can be referred to as the convolution kernel. The output may be referred to as the feature map. For example, the input to a convolution layer can be a multidimensional array of data that defines the various color components of an input image. The convolution kernel can be a multidimensional array of parameters, where the parameters are adapted by the training process for the neural network.

Recurrent neural networks (RNNs) are a family of feedforward neural networks that include feedback connections between layers. RNNs enable modeling of sequential data by sharing parameter data across different parts of the neural network. The architecture for a RNN includes cycles. The cycles represent the influence of a present value of a variable on its own value at a future time, as at least a portion of the output data from the RNN is used as feedback for processing subsequent input in a sequence. This feature makes RNNs particularly useful for language processing due to the variable nature in which language data can be composed.

The figures described herein present exemplary feedforward, CNN, and RNN networks, as well as describe a general process for respectively training and deploying each of those types of networks. It will be understood that these descriptions are exemplary and non-limiting as to any specific embodiment described herein and the concepts illustrated can be applied generally to deep neural networks and machine learning techniques in general.

The exemplary neural networks described above can be used to perform deep learning. Deep learning is machine learning using deep neural networks. The deep neural networks used in deep learning are artificial neural networks composed of multiple hidden layers, as opposed to shallow neural networks that include only a single hidden layer. Deeper neural networks are generally more computationally intensive to train. However, the additional hidden layers of the network enable multistep pattern recognition that results in reduced output error relative to shallow machine learning techniques.

Deep neural networks used in deep learning typically include a front-end network to perform feature recognition coupled to a back-end network which represents a mathematical model that can perform operations (e.g., object classification, speech recognition, etc.) based on the feature representation provided to the model. Deep learning enables machine learning to be performed without requiring hand crafted feature engineering to be performed for the model. Instead, deep neural networks can learn features based on statistical structure or correlation within the input data. The learned features can be provided to a mathematical model that can map detected features to an output. The mathematical model used by the network is generally specialized for the specific task to be performed, and different models will be used to perform different task.

Once the neural network is structured, a learning model can be applied to the network to train the network to perform specific tasks. The learning model describes how to adjust the weights within the model to reduce the output error of the network. Backpropagation of errors is a common method used to train neural networks. An input vector is presented to the network for processing. The output of the network is compared to the desired output using a loss function and an error value is calculated for each of the neurons in the output layer. The error values are then propagated backwards until each neuron has an associated error value which roughly represents its contribution to the original output. The network can then learn from those errors using an algorithm, such as the stochastic gradient descent algorithm, to update the weights of the of the neural network.

Figure 13:
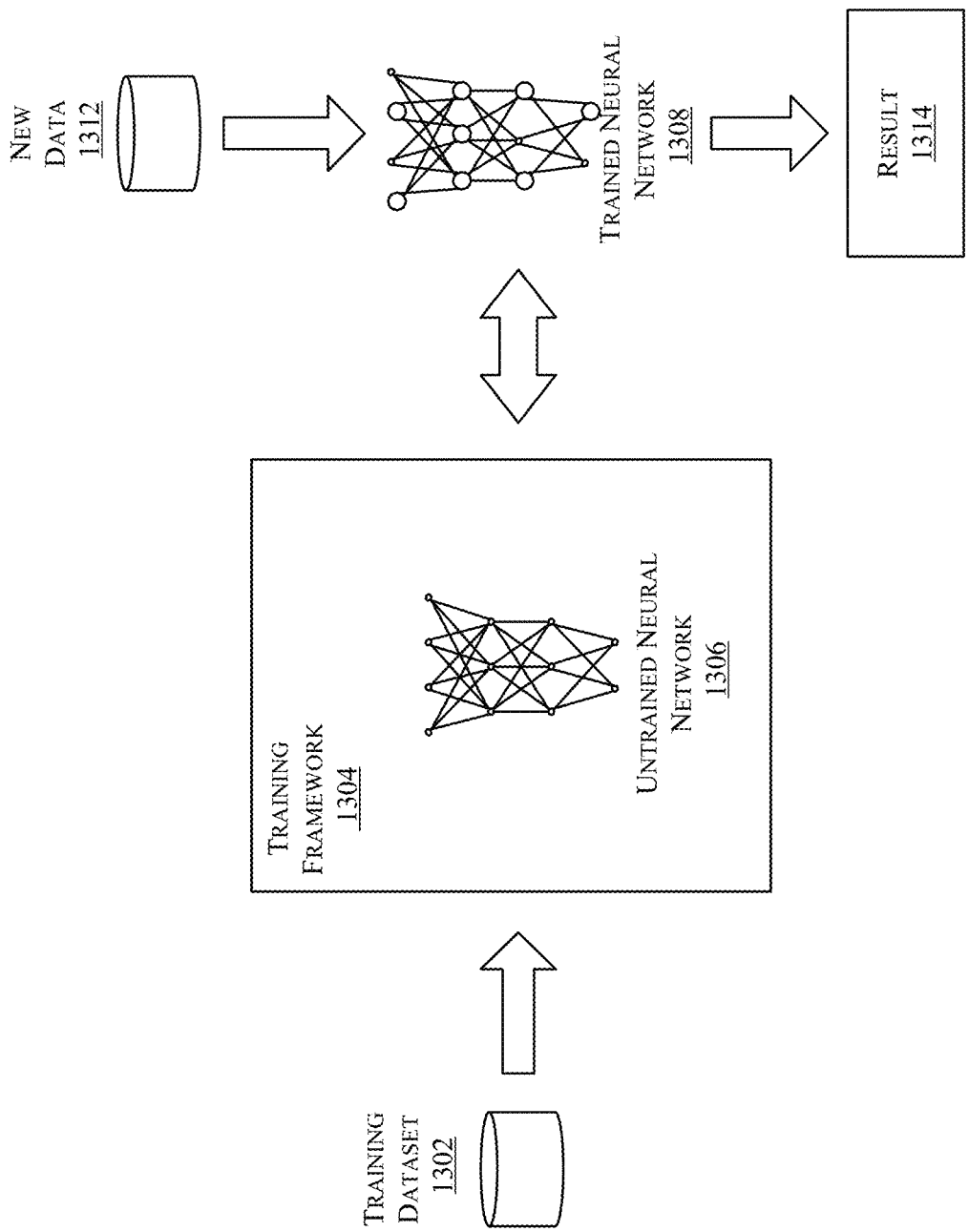
FIG. 13 illustrates training and deployment of a deep neural network in accordance with one or more embodiments.

FIG. 13 illustrates training and deployment of a deep neural network. Once a given network has been structured for a task the neural network is trained using a training dataset 1302. Various training frameworks have been developed to enable hardware acceleration of the training process. For example, the machine learning framework 1204 of FIG. 12 may be configured as a training framework 1304. The training framework 1304 can hook into an untrained neural network 1306 and enable the untrained neural net to be trained using the parallel processing resources described herein to generate a trained neural network 1308. To start the training process the initial weights may be chosen randomly or by pre-training using a deep belief network. The training cycle then be performed in either a supervised or unsupervised manner.

Supervised learning is a learning method in which training is performed as a mediated operation, such as when the training dataset 1302 includes input paired with the desired output for the input, or where the training dataset includes input having known output and the output of the neural network is manually graded. The network processes the inputs and compares the resulting outputs against a set of expected or desired outputs. Errors are then propagated back through the system. The training framework 1304 can adjust to adjust the weights that control the untrained neural network 1306. The training framework 1304 can provide tools to monitor how well the untrained neural network 1306 is converging towards a model suitable to generating correct answers based on known input data. The training process occurs repeatedly as the weights of the network are adjusted to refine the output generated by the neural network. The training process can continue until the neural network reaches a statistically desired accuracy associated with a trained neural network 1308. The trained neural network 1308 can then be deployed to implement any number of machine learning operations.

Unsupervised learning is a learning method in which the network attempts to train itself using unlabeled data. Thus, for unsupervised learning the training dataset 1302 will include input data without any associated output data. The untrained neural network 1306 can learn groupings within the unlabeled input and can determine how individual inputs are related to the overall dataset. Unsupervised training can be used to generate a self-organizing map, which is a type of trained neural network 1307 capable of performing operations useful in reducing the dimensionality of data. Unsupervised training can also be used to perform anomaly detection, which allows the identification of data points in an input dataset that deviate from the normal patterns of the data.

Variations on supervised and unsupervised training may also be employed. Semi-supervised learning is a technique in which in the training dataset 1302 includes a mix of labeled and unlabeled data of the same distribution. Incremental learning is a variant of supervised learning in which input data is continuously used to further train the model. Incremental learning enables the trained neural network 1308 to adapt to the new data 1312 without forgetting the knowledge instilled within the network during initial training.

Whether supervised or unsupervised, the training process for particularly deep neural networks may be too computationally intensive for a single compute node. Instead of using a single compute node, a distributed network of computational nodes can be used to accelerate the training process.

The following examples pertain to further embodiments.

Example 1 is a system for emotional adaptive driving policies for automated driving vehicles, comprising a first plurality of sensors to detect environmental information relating to at least one passenger in a vehicle; and a controller communicatively coupled to the plurality of sensors and comprising processing circuitry, to receive the environmental information from the first plurality of sensors; determine, from the environmental information, an emotional state of the at least one passenger; and implement a driving policy based at least in part on the emotional state of the at least one passenger.

Example 2 may comprise the subject matter of any previous claim, wherein the plurality of sensors comprises at least one of a camera sensor, a microphone sensor, or a biometric sensor.

Example 3 may comprise the subject matter of any previous claim, wherein the controller comprises processing circuitry to implement a heart rate emotion classifier to determine the emotional state of the at least one passenger from an input representative of the heart rate of the at least one passenger; an audio emotion classifier to determine the emotional state of the at least one passenger from an input representative of an audio output of the at least one passenger; a semantics emotion classifier to determine the emotional state of the at least one passenger from an input representative of semantics of an audio output of the at least one passenger; and a computer vision emotion classifier to determine the emotional state of the at least one passenger from an output of the camera sensor.

Example 4 may comprise the subject matter of any previous claim, further comprising a second plurality of sensors to detect context information relating to the environment surrounding the vehicle, wherein the plurality of sensors comprises at least one of a video sensor, a RADAR sensor, a LIDAR sensor, an inertial measurement unit (IMU) sensor, and a global navigational satellite system (GNSS) sensor.

Example 5 may comprise the subject matter of any previous claim, wherein the controller comprises processing circuitry to implement a sensor based object recognition module to identify one or more objects proximate the vehicle based on inputs from the second plurality of sensors; and a localization module to determine a location of the vehicle based on inputs from at least one of the IMU sensor or the GNSS sensor.

Example 6 may comprise the subject matter of any previous claim, further comprising processing circuitry to implement a driving policy engine to generate a trajectory for the vehicle.

Example 7 may comprise the subject matter of any previous claim, wherein the driving policy engine comprises a semantic understanding module; a trajectory generation module; and a trajectory monitoring module.

Example 8 may comprise the subject matter of any previous claim, wherein the driving policy engine comprises a data store comprising emotion rules: a data store comprising traffic rules; a path planning module; and a trajectory generation and monitoring module.

Example 9 may comprise the subject matter of any previous claim, wherein the driving policy engine executes logic, at least partially including hardware logic, to determine a current trajectory for the vehicle; generate an updated trajectory for the vehicle based at least in part on an emotional state of the at least one passenger; execute a maneuver based on the updated trajectory; and alter the updated trajectory in response to a change in the emotional state of the at least one passenger.

Example 10 may comprise the subject matter of any previous claim, wherein the driving policy engine comprises a neural network model programmed to maximize a reward function based at least in part on the emotional state of the at least one passenger.

Example 11 is a vehicle control system comprising a first plurality of sensors to detect environmental information relating to at least one passenger in a vehicle; and a controller communicatively coupled to the plurality of sensors and comprising processing circuitry, to receive the environmental information from the first plurality of sensors; determine, from the environmental information, an emotional state of the at least one passenger; and implement a driving policy based at least in part on the emotional state of the at least one passenger; and a vehicle actuation module comprising a plurality of actuators to execute the driving policy.

Example 12 may comprise the subject matter of any previous claim, wherein the plurality of sensors comprises at least one of a camera sensor, a microphone sensor, or a biometric sensor.

Example 13 may comprise the subject matter of any previous claim, wherein the controller comprises processing circuitry to implement: a heart rate emotion classifier to determine the emotional state of the at least one passenger from an input representative of the heart rate of the at least one passenger; an audio emotion classifier to determine the emotional state of the at least one passenger from an input representative of an audio output of the at least one passenger; a semantics emotion classifier to determine the emotional state of the at least one passenger from an input representative of semantics of an audio output of the at least one passenger; and a computer vision emotion classifier to determine the emotional state of the at least one passenger from an output of the camera sensor.

Example 14 may comprise the subject matter of any previous claim, further comprising a second plurality of sensors to detect context information relating to the environment surrounding the vehicle, wherein the plurality of sensors comprises at least one of a video sensor, a RADAR sensor, a LIDAR sensor, an inertial measurement unit (IMU) sensor, and a global navigational satellite system (GNSS) sensor.

Example 15 may comprise the subject matter of any previous claim, wherein the controller comprises processing circuitry to implement a sensor based object recognition module to identify one or more objects proximate the vehicle based on inputs from the second plurality of sensors; and localization module to determine a location of the vehicle based on inputs from at least one of the IMU sensor or the GNSS sensor.

Example 16 may comprise the subject matter of any previous claim, further comprising processing circuitry to implement a driving policy engine to generate a trajectory for the vehicle.

Example 17 may comprise the subject matter of any previous claim, wherein the driving policy engine comprises a semantic understanding module; a trajectory generation module; and a trajectory monitoring module.

Example 18 may comprise the subject matter of any previous claim, wherein the driving policy engine comprises a data store comprising emotion rules; a data store comprising traffic rules; a path planning module; and trajectory generation and monitoring module.

Example 19 may comprise the subject matter of any previous claim, wherein the driving policy engine executes logic, at least partially including hardware logic, to determine a current trajectory for the vehicle; generate an updated trajectory for the vehicle based at least in part on an emotional state of the at least one passenger; execute a maneuver based on the updated trajectory; and alter the updated trajectory in response to a change in the emotional state of the at least one passenger.

Example 20 may comprise the subject matter of any previous claim, wherein the driving policy engine comprises a neural network model programmed to maximize a reward function based at least in part on the emotional state of the at least one passenger.

In various embodiments, the operations discussed herein, e.g., with reference to the figures described herein, may be implemented as hardware (e.g., logic circuitry), software, firmware, or combinations thereof, which may be provided as a computer program product, e.g., including a tangible (e.g., non-transitory) machine-readable or computer-readable medium having stored thereon instructions (or software procedures) used to program a computer to perform a process discussed herein. The machine-readable medium may include a storage device such as those discussed with respect to the present figures.

Additionally, such computer-readable media may be downloaded as a computer program product, wherein the program may be transferred from a remote computer (e.g., a server) to a requesting computer (e.g., a client) by way of data signals provided in a carrier wave or other propagation medium via a communication link (e.g., a bus, a modem, or a network connection).

Reference in the specification to "one embodiment" or "an embodiment" means that a particular feature, structure, and/or characteristic described in connection with the embodiment may be included in at least an implementation. The appearances of the phrase "in one embodiment" in various places in the specification may or may not be all referring to the same embodiment.

Also, in the description and claims, the terms "coupled" and "connected," along with their derivatives, may be used. In some embodiments, "connected" may be used to indicate that two or more elements are in direct physical or electrical contact with each other. "Coupled" may mean that two or more elements are in direct physical or electrical contact. However, "coupled" may also mean that two or more elements may not be in direct contact with each other, but may still cooperate or interact with each other.

Thus, although embodiments have been described in language specific to structural features and/or methodological acts, it is to be understood that claimed subject matter may not be limited to the specific features or acts described. Rather, the specific features and acts are disclosed as sample forms of implementing the claimed subject matter.

What is claimed is:

1. A system for emotional adaptive driving policies for automated driving vehicles, comprising:
    a first plurality of sensors configured to detect environmental information relating to at least one occupant in a vehicle; and
    a controller communicatively coupled to the first plurality of sensors and comprising processing circuitry configured to:
        receive the environmental information from the first plurality of sensors;
        determine, from the environmental information, an emotional state of the at least one occupant; and
        implement a driving policy based at least in part on the emotional state of the at least one occupant,
    wherein the driving policy defines a set of environment observations including the environmental information, and a set of actions to be applied by an automated driving vehicle to execute driving maneuvers in response to road events in accordance with one or more control parameters, and
    wherein the one or more control parameters are adjusted based upon the emotional state of the at least one occupant.

2. The system of claim 1, wherein the first plurality of sensors comprises at least one of a camera sensor, a microphone sensor, or a biometric sensor.

3. The system of claim 2, wherein the controller comprises processing circuitry configured to implement:
    a heart rate emotion classifier to determine the emotional state of the at least one occupant from an input representative of the heart rate of the at least one occupant;
    an audio emotion classifier to determine the emotional state of the at least one occupant from an input representative of an audio output of the at least one occupant;
    a semantics emotion classifier to determine the emotional state of the at least one occupant from an input representative of semantics of an audio output of the at least one occupant; and
    a computer vision emotion classifier to determine the emotional state of the at least one occupant from an output of the camera sensor.

4. The system of claim 3, further comprising:
    a second plurality of sensors configured to detect context information relating to the environment surrounding the vehicle,
    wherein the second plurality of sensors comprises at least one of a video sensor, a RADAR sensor, a LIDAR sensor, an inertial measurement unit (IMU) sensor, or a global navigational satellite system (GNSS) sensor.

5. The system of claim 4, wherein the controller comprises processing circuitry configured to implement:
a sensor based object recognition module to identify one or more objects proximate to the vehicle based on inputs from the second plurality of sensors; and
a localization module to determine a location of the vehicle based on inputs from at least one of the IMU sensor or the GNSS sensor.

6. The system of claim 5, further comprising:
processing circuitry configured to implement a driving policy engine to generate a trajectory for the vehicle.

7. The system of claim 6, wherein the driving policy engine comprises:
a semantic understanding module;
a trajectory generation module; and
a trajectory monitoring module.

8. The system of claim 6, wherein the driving policy engine comprises:
a data store comprising emotion rules:
a data store comprising traffic rules;
a path planning module; and
a trajectory generation and monitoring module.

9. The system of claim 6, wherein the driving policy engine executes logic, at least partially including hardware logic, to:
determine a current trajectory for the vehicle;
generate an updated trajectory for the vehicle based at least in part on an emotional state of the at least one occupant;
execute a maneuver based on the updated trajectory; and
alter the updated trajectory in response to a change in the emotional state of the at least one occupant.

10. The system of claim 6, wherein the driving policy engine comprises:
a neural network model programmed to maximize a reward function based at least in part on the emotional state of the at least one occupant.

11. A vehicle control system comprising:
a first plurality of sensors configured to detect environmental information relating to at least one occupant in a vehicle; and
a controller communicatively coupled to the first plurality of sensors and comprising processing circuitry configured to:
receive the environmental information from the first plurality of sensors;
determine, from the environmental information, an emotional state of the at least one occupant; and
implement a driving policy based at least in part on the emotional state of the at least one occupant; and
a vehicle actuation module comprising a plurality of actuators configured to execute the driving policy,
wherein the driving policy defines a set of environment observations including the environmental information, and a set of actions to be applied by an automated driving vehicle to execute driving maneuvers in response to road events in accordance with one or more control parameters, and
wherein the one or more control parameters are adjusted based upon the emotional state of the at least one occupant.

12. The system of claim 11, wherein the first plurality of sensors comprises at least one of a camera sensor, a microphone sensor, or a biometric sensor.

13. The system of claim 12, wherein the controller comprises processing circuitry configured to implement:
a heart rate emotion classifier to determine the emotional state of the at least one occupant from an input representative of the heart rate of the at least one occupant;
an audio emotion classifier to determine the emotional state of the at least one occupant from an input representative of an audio output of the at least one occupant;
a semantics emotion classifier to determine the emotional state of the at least one occupant from an input representative of semantics of an audio output of the at least one occupant; and
a computer vision emotion classifier to determine the emotional state of the at least one occupant from an output of the camera sensor.

14. The system of claim 13, further comprising:
a second plurality of sensors to detect context information relating to the environment surrounding the vehicle,
wherein the second plurality of sensors comprises at least one of a video sensor, a RADAR sensor, a LIDAR sensor, an inertial measurement unit (IMU) sensor, or a global navigational satellite system (GNSS) sensor.

15. The system of claim 14, wherein the controller comprises processing circuitry configured to implement:
a sensor based object recognition module to identify one or more objects proximate to the vehicle based on inputs from the second plurality of sensors; and
a localization module to determine a location of the vehicle based on inputs from at least one of the IMU sensor or the GNSS sensor.

16. The system of claim 15, further comprising:
processing circuitry configured to implement a driving policy engine to generate a trajectory for the vehicle.

17. The system of claim 16, wherein the driving policy engine comprises:
a semantic understanding module;
a trajectory generation module; and
a trajectory monitoring module.

18. The system of claim 16, wherein the driving policy engine comprises:
a data store comprising emotion rules:
a data store comprising traffic rules;
a path planning module; and
a trajectory generation and monitoring module.

19. The system of claim 16, wherein the driving policy engine executes logic, at least partially including hardware logic, to:
determine a current trajectory for the vehicle;
generate an updated trajectory for the vehicle based at least in part on an emotional state of the at least one occupant;
execute a maneuver based on the updated trajectory; and
alter the updated trajectory in response to a change in the emotional state of the at least one occupant.

20. The system of claim 16, wherein the driving policy engine comprises:
a neural network model programmed to maximize a reward function based at least in part on the emotional state of the at least one occupant.

21. The system of claim 1, wherein the controller is further configured to adjust the driving policy by adjusting the one or more control parameters based upon the emotional state of the at least one occupant such that the same driving maneuver from among the set of driving maneuvers is executed differently for different respective emotional states of the occupant.

22. The system of claim 1, wherein the environmental information received from the first plurality of sensors is associated with a plurality of vehicle occupants including the at least one occupant, and
> wherein the emotional state of the at least one occupant is determined based upon (i) the reaction of the at least one occupant, and (ii) a reaction between the at least one occupant and at least another occupant from among the plurality of vehicle occupants.

23. The system of claim 1, wherein the controller is further configured to extract, from the environmental information, content of speech spoken by the at least one occupant, and to determine an emotional state of the at least one occupant based upon the content of the speech.

\* \* \* \* \*